US012716052B2

(12) United States Patent
Lahann et al.

(10) Patent No.: US 12,716,052 B2
(45) Date of Patent: Aug. 25, 2026

(54) ENGINEERED FIBRILLAR EXTRACELLULAR MATRIX NETWORKS FOR THREE-DIMENSIONAL (3D) CELLULAR SUPPORT SYSTEMS

(71) Applicant: THE REGENTS OF THE UNIVERSITY OF MICHIGAN, Ann Arbor, MI (US)

(72) Inventors: Joerg Lahann, Ann Arbor, MI (US); Mirella Wawryszyn, Lampertheim (DE); Dylan B. Neale, Somerville, MA (US)

(73) Assignee: The Regents of The University of Michigan, Ann Arbor, MI (US)

(*) Notice: Subject to any disclaimer, the term of this patent is extended or adjusted under 35 U.S.C. 154(b) by 642 days.

(21) Appl. No.: 18/143,871

(22) Filed: May 5, 2023

(65) Prior Publication Data

US 2023/0357710 A1 Nov. 9, 2023

Related U.S. Application Data

(60) Provisional application No. 63/339,335, filed on May 6, 2022.

(51) Int. Cl.
*C12N 5/00* (2006.01)

(52) U.S. Cl.
CPC ........ *C12N 5/0062* (2013.01); *C12N 2513/00* (2013.01); *C12N 2533/14* (2013.01); *C12N 2533/40* (2013.01); *C12N 2533/52* (2013.01); *C12N 2533/78* (2013.01); *C12N 2535/00* (2013.01)

(58) Field of Classification Search
CPC .............. C12N 5/0062; C12N 2513/00; C12N 2533/14; C12N 2533/40; C12N 2533/52; C12N 2533/78; C12N 2535/00; C12N 2533/54; C12N 2533/70; C12N 2533/80; C12N 2533/90; C12N 5/0068
See application file for complete search history.

(56) References Cited

U.S. PATENT DOCUMENTS

| | | | |
|---|---|---|---|
| 3,959,079 A | 5/1976 | Mareschi et al. | |
| 5,858,721 A | 1/1999 | Naughton et al. | |
| 8,039,258 B2 | 10/2011 | Harris et al. | |
| 11,479,753 B2 | 10/2022 | Ramcharan et al. | |
| 2006/0252981 A1 | 11/2006 | Matsuda et al. | |
| 2008/0194010 A1 | 8/2008 | Liu | |
| 2009/0043079 A1 | 2/2009 | Chen et al. | |
| 2009/0148486 A1 | 6/2009 | Lu et al. | |
| 2009/0238853 A1 | 9/2009 | Liu et al. | |
| 2010/0119575 A1 | 5/2010 | Scharnweber et al. | |
| 2013/0288375 A1* | 10/2013 | Zhang | C12N 5/0671 435/395 |
| 2015/0037432 A1 | 2/2015 | Malinin | |
| 2018/0313822 A1 | 11/2018 | Murphy et al. | |
| 2019/0144818 A1 | 5/2019 | Ramcharan et al. | |
| 2020/0046881 A1 | 2/2020 | Raimondi et al. | |
| 2021/0046213 A1 | 2/2021 | Timnak et al. | |

FOREIGN PATENT DOCUMENTS

| | | |
|---|---|---|
| EP | 0097907 A2 | 1/1984 |
| JP | 2012213390 A | 11/2012 |
| WO | WO-2012094611 A1 | 7/2012 |
| WO | WO-2013040078 A2 | 3/2013 |
| WO | WO-2015005349 A1 | 1/2015 |
| WO | WO-2016042211 A1 | 3/2016 |

OTHER PUBLICATIONS

Bian, S., He, M., Sui, J., Cai, H., Sun, Y., Liang, J., Fan, Y. and Zhang, X., 2016. The self-crosslinking smart hyaluronic acid hydrogels as injectable three-dimensional scaffolds for cells culture. Colloids and Surfaces B: Biointerfaces, 140, pp. 392-402. (Year: 2016).*

Acevedo-Acevedo, Suehelay et al.; "Substrate stiffness effect and chromosome missegregation in hIPS cells"; Journal of Negative Results in BioMedicine (2015) 14:22; 7 pages.

Auvinen, Paivi et al.; "Hyaluronan in Peritumoral Stroma and Malignant Cells Associates with Breast Cancer Spreading and Predicts Survival"; American Journal of Pathology, vol. 156, No. 2; Feb. 2000; pp. 529-536.

Auvinen, Paivi et al.; "Increased hyaluronan content and stromal cell CD44 associate with HER2 positivity and poor prognosis in human breast cancer"; International Journal of Cancer, 132; 2013; pp. 531-539.

Baker, Brendon M. et al.; "Cell-mediated fibre recruitment drives extracellular matrix mechanosensing in engineered fibrillar microenvironments"; Nature Materials, vol. 14; Dec. 2015; 10 pages.

Bergman, Kristoffer et al.; "Hyaluronic Acid Derivatives Prepared in Aquious Media by Triazine-activated Amidation"; Biomacromolecules, vol. 8, No. 7; 2007; pp. 2190-2195.

(Continued)

*Primary Examiner* — Jeremy C Flinders
*Assistant Examiner* — Masudur Rahman
(74) *Attorney, Agent, or Firm* — Harness, Dickey & Pierce, P.L.C.

(57) ABSTRACT

Synthetic cellular support systems in the form of engineered extracellular matrices are provided. The cellular support system may include a three-dimensional scaffold structure comprising at least one void. At least one suspended fibril spans across the at least one void in the three-dimensional scaffold structure. The suspended fibril comprises at least one extracellular matrix protein, such as fibronectin, and at least one glycan, such as a hyaluronic acid. The suspended fibril is capable of supporting cells and promoting three-dimensional cellular growth. In various aspects, a plurality of suspended fibrils may span the void to form a three-dimensional suspended fibrillar network.

21 Claims, 12 Drawing Sheets

(56) References Cited

OTHER PUBLICATIONS

Figures 1A, 1B, 1C, 1D, 1E, 1F:
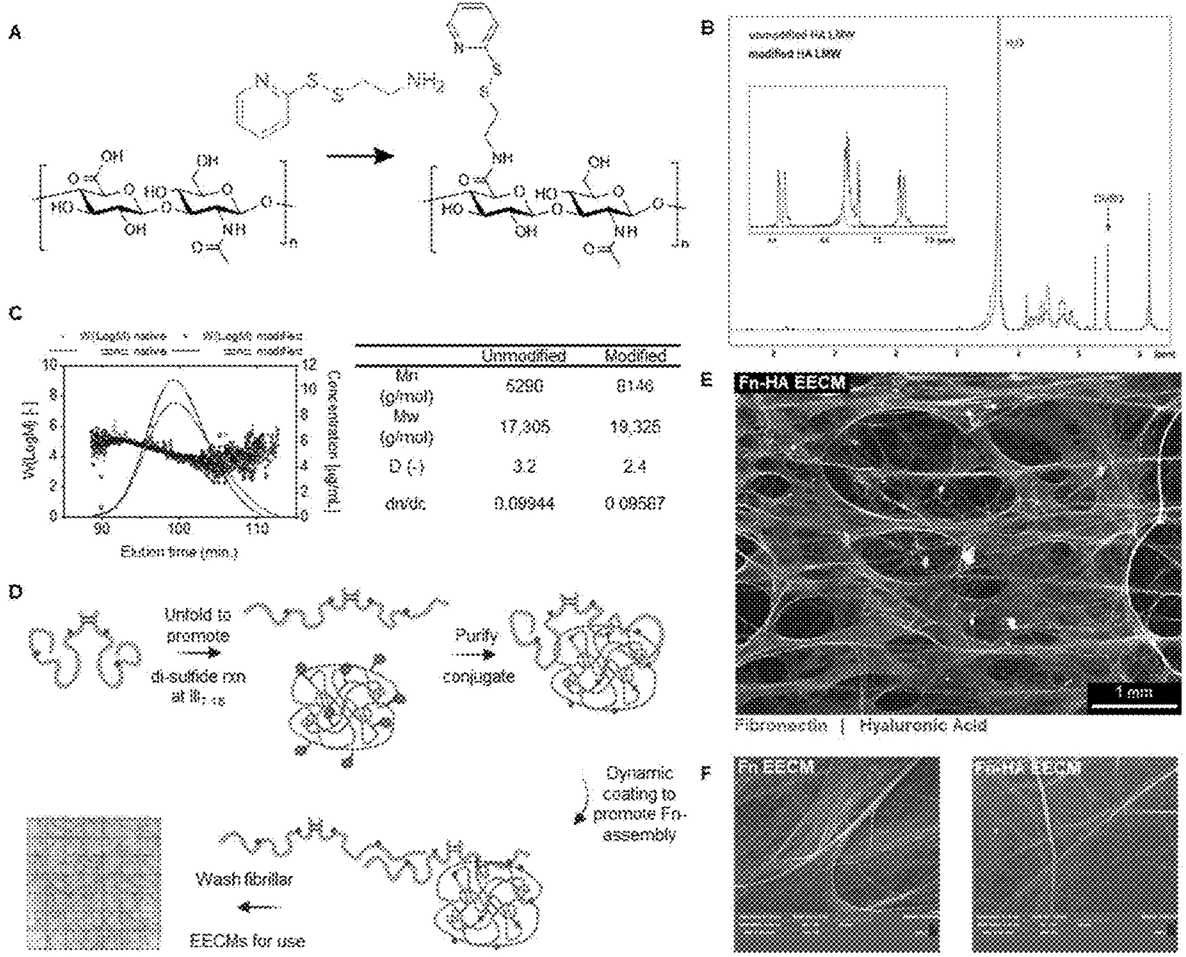

Budday, Silvia et al.; "Fifty Shades of Brain: A Review on the Mechanical Testing and Modeling of Brain Tissue"; Archives of Computational Methods in Engineering (2020) 27; https://doi.org/10.1007/s11831-019-09352-w; pp. 1187-1230.
Mao, Yong et al.; "Fibronectin fibrillogenesis, a cell-mediated matrix assembly process"; Elsevier B.V./International Society of Matrix Biology 24 (2005); pp. 389-399.
Seo, Bo Ri et al.; "Obesity-dependent changes in interstitial ECM mechanics promote breast tumorigenesis"; Science Translational Medicine, vol. 7, Issue 301; Aug. 19, 2015; 12 pages.
Shinde, Aparna et al.; "Autocrine Fibronectin Inhibits breast Cancer Metastasis" Molecular Cancer Research, 16 (10); www.aacrjournals.org; Oct. 2018; pp. 1579-1589.
Soofi, Shauheen S. et al.; "The elastic modulus of Matrigel as determined by atomic force microscopy"; Journal of Structural Biology, 167; (2009); pp. 216-219.
Sottile, Jane et al.; "Fibronectin Polymerization Regulates the Composition and Stability of Extracellular Matrix Fibrils and Cell-Matrix Adhesions"; Molecular Biology of the Cell, vol. 13; Oct. 2002; pp. 3546-3559.
Stanisavljevic, Jelena et al.; "Snail1-Expressing Fibroblasts in the Tumor Microenvironment Display Mechanical Properties That Support Metastasis"; Cancer Research, 75(2); www.aacrjournals.org; Jan. 15, 2015; pp. 284-295.
Steier, Anke et al.; "Emerging Trends in Information-Driven Engineering of Complex Biological System"; Advanced Materials, 2019, 31; 22 pages.
Seidlits, S. K. et al., "Fibronectin-hyaluronic acid composite hydrogels for three-dimensional endothelial cell culture", Acta Biomaterialia, Mar. 23, 2011 (Online publication date), vol. 7, pp. 2401-2409.
International Search Report and Written Opinion for PCT Application No. PCT/US2023/021147 issued Sep. 8, 2023; 11 pages.
Extended European Search Report for European Patent Application No. 17796855.9 dated Nov. 14, 2019, 9 pages.
International Search Report and Written Opinion issued in PCT/US2017/032197, dated May 11, 2017; ISA/US.
Ahmed, Z. et al., "Nerve Guide Material Made from Fibronectin Assessment of in Vitro Properties," <i>Tissue Engineering </i>(2003), 9, 2, pp. 219-231.
Ahmed, Zubair et al., "Stabilization of fibronectin mats with micromolar concentrations of copper," <i>Biomaterials </i>(1999), 20, pp. 201-209.
Ahn, Seungkuk et al., "Self-Organizing Large-Scale Extracellular-Matrix Protein Networks," <i>Adv. Mater. < /i>(Mar. 31, 2015), 27, pp. 2838-2845.
Baneyx, Gretchen et al., "Fibronectin extension and unfolding within cell matrix fibrils controlled by cytoskeletal tension," <i>PNAS </i>(Apr. 16, 2002), 99, 8, pp. 5139-5143.
Bergmann, K. et al., "Hyaluronic Acid Derivatives Prepared in Aqueous Media by Triazine-Activated Amidation"; Biomacromolecules 8(7); Jun. 19, 2007; pp. 2190-2195.
Bhaskar, Srijanani et al., "Microstructured Materials Based on Multicompartmental Fibers," <i>JACS </i>(Apr. 29, 2009), 131, 19, pp. 6650-6651.
Brown, Robert A. et al., "Preparation of orientated fibrous mats from fibronectin: composition and stability," <i>Biomaterials </i>(1994), 15, 6, pp. 457-464.
Capulli, A.K. et al.,: "Fibrous scaffolds for building hearts and heart parts", Advanced Drug Delivery Reviews, vol. 96, pp. 83-102 (Published online Dec. 4, 2015); ISSN: 0169-409X; DOI: 10.1016/J.ADDR.2015.11.020.
Chang et al., "A laminin 511 matrix is regulated by TAZ and functions as the ligand for the alpha6Bbeta1 integrin to sustain breast cancer stem cells," <i>Molecular, Cell and Cancer Biology Publications </i>(2015), 22, 9 pages.
Chen et al. Culturing of skin fibroblasts in a thin PLGA—collagen hybrid mesh. Biomaterials 26 (2005) 2559-2566 (Year: 2005).
Deravi, Leila F. et al., "Differential Contributions of Conformation Extension and Domain Unfolding to Properties of Fibronectin Nanotextiles," <i>Nano Lett. < /i>(Oct. 8, 2012), 12, pp. 5587-5592.
Ejim, Obiora S. et al., "Production of artificial-orientated mats and strands from plasm fibronectin: a morphological study," <i>Biomaterials </i>(1993), 1, 10, pp. 743-748.
Flynn, L.E., "The use of decellularized adipose tissue to provide an inductive microenvironment for the adipogenic differentiation of human adipose-derived stem cells," <i>Biomaterials </i>(2010), 31, pp. 4715-4724.
Ginestier, et al., "ALDH1 Is a Marker of Normal and Malignant Human Mammary Stem Cells and a Predictor of Poor Clinical Outcome," <i>Cell Stem Cell </i>(Nov. 14, 2007), 1, pp. 555-567 (2007).
Guan, Jingjiao et al., "Simultaneous fabrication of hybrid arrays of nanowires and micro/nanoparticles by dewetting on micropillars," <i>Soft Matter</i>, (Aug. 31, 2007), 3, pp. 1369-1371.
Jordahl, Stacy et al.; "Engineered Fibrillar Fibronectin Networks as Three-Dimensional Tissue Scaffolds;" Advanced Materials Communication 31(16); (Nov. 15, 2019, first published Sep. 30, 2019); (https://doi.org/10.1002/adma.201904580); 10 pages.
Kaiser, Peter et al., "Differential adhesion of fibroblast and neuroblastoma cells on size- and geometry-controlled nanofibrils of the extracellular matrix," <i>Soft Matter </i>(Oct. 12, 2009), 6, pp. 113-119.
Kaity, Santanu et al., "Microsponges: A Novel Strateg for Drug Delivery System"; Journal of Advanced Pharmaceutical Technology and Research; Jul.-Sep. 2010; vol. 1; Issue 3; pp. 283-290.
Klotzsch, Enrico et al., "Fibronectin forms the most extensible biological fibers displaying switchable force-exposed cryptic binding sites," <i>PNAS </i>(Oct. 27, 2009), 106, 43, pp. 18267-18272.
Lee, Jungwoo et al., "Three-Dimensional Cell Culture Matrices: State of the Art," <i>Tissue Engineering: Part B </i>(2008), 14, 1, pp. 61-86.
Li, D. et al., "Electrospinning Nanofibers as Uniaxially Aligned Arrays and Layer-by-Layer Stacked Films," Advanced Materials, vol. 16, No. 4, pp. 361-366 (Published Feb. 17, 2014); ISSN: 0935-9648; DOI: 10.1002/ADMA.200306226.
Little, William C. et al., "Assay to mechanically tune and optically probed fibrillar fibronectin conformations from fully relaxed to breakage," <i>Matrix Biology </i>(2008), 27, pp. 451-461.
Lodish et al. Section 22.3 Collagen: The Fibrous Proteins of the Matrix. Molecular Cell Biology. 4th edition. New York: W.H. Freeman. p. 1-6 (Year: 2000).
Mao, Yong et al., "Fibronectin fibrillogenesis, a cell-mediated matrix assembly process," <i>Matrix Biology </i>(2005), 24, pp. 389-399.
Mitsi, Maria et al., "The ultrastructure of fibronectin fibers pulled from a protein monolayer at the air-liquid interface and the mechanism of the sheet-to-fiber transition," <i>Biomaterials </i>(Oct. 13, 2014), 36, pp. 66-79.
Oberdörfer, York et al., "Conformational Analysis of Native Fibronectin by Means of Force Spectroscopy," <i>Langmuir </i>(2000), 76, pp. 9955-9958.
Pabba, Santosh et al., "Biopolymerization-driven self-assembly of nanofiber air-bridges," <i>Soft Matter </i>(Feb. 3, 2009), 5, pp. 1378-1385.
Paget, Stephen, "The Distribution of Secondary Growths in Cancer of the Breast," <i>The Lancet </i>(Mar. 23, 1889), 133, 3421, pp. 571-573.
Pham, Quynh P. et al., "Electrospinning of Polymeric Nanofibers for Tissue Engineering Application: A Review," <i>Tissue Engineering</i>, (2006), 12, 5, pp. 1197-1211.
Sabater i Serra, Roser et al., "Role of chemical crosslinking in material-driven assembly of fibronectin (nano)networks: 2D surfaces and 3D scaffolds," Colloids and Surfaces. B: Biointerfaces, vol. 148 (Published Jan. 31, 2016), pp. 324-332; ISSN: 0927-7765; DOI: 10.1016/J.COLSURFB.2016.08.044.
Schwarzbauer, Jean E. et al., "Fibronectin fibrillogenesis: a paradigm for extracellular matrix assembly," <i>Curr. Opin. Cell Biol. < /i>(1999), 11, pp. 622-627.

(56) References Cited

OTHER PUBLICATIONS

Simon, Karen A. et al., "Polymer-based mesh as supports for multi-layered 3D cell culture and assays" <i>Biomaterials </i>(Oct. 2, 2013), 35, 1, pp. 259-268.

Steier, A. et al.; "Emerging Trends in Information-Driven engineering of complex Biological Systems"; Advanced Materials 31; Apr. 8, 2019; 22 pages.

Ulmer, J., Geiger, B. & Spatz, J.P. Force-induced fibronectin fibrillogenesis in vitro. Soft Matter 4, 1998-2007 (2008).

Wierzbicka-Patynowski, Iwona et al., "The ins and outs of fibronectin matrix assembly," <i>Journal of Cell Science</i>, (Aug. 15, 2003), 116, pp. 3269-3276.

https://en.wiktionary.org/wiki/microsponge <https://protect-us.mimecast.com/s/fLobCERZ81HlojGwcNLUvF>; accessed on Jan. 12, 2022; 1 page.

Yoo, Sang Jin et al., "Simple and Novel Three Dimensional Neuronal Cell Culture Using a Micro Mesh Scaffold," <i>Experimental Neurobiology </i>(Jun. 2011), 20, 2, pp. 110-115.

Zhang et al. Influence of surgical suture properties on the tribological interactions with artificial skin by a capstan experiment approach. Friction 5(1): 87-98 (2017) (Year: 2017).

* cited by examiner

*$^1$H NMR spectrum of 14% degree of substitution modification of 2000kDa HA (hmw HA-2PT) and 15kDa (lmw HA-2PT).*

| Mass loading | HA in Rxn (% m/m) | Measured HA (% m/m) | stdev (%m/m) | n |
|---|---|---|---|---|
| Fn-HA$_{2000k}$ | 66 | 61.1 | ±2.9 | 11 |
| Fn-HA$_{15k}$ | 66 | 67.5 | ±2.1 | 9 |
| **Fiber diameter** | **Mean diameter (μm)** | **+s / -s (μm)** | **95% range (μm)** | **n** |
| Fn-HA$_{2000k}$ | 1.2 | +0.75 / -0.34 | 0.65 - 3.71 | 240 |
| Fn-HA$_{15k}$ | 1.09 | + 0.72 / -0.32 | 0.63 ~ 4.19 | 240 |
| Fn | 1.23 | + 0.9 / 0.36 | 0.63 ~ 4.19 | 240 |

| Mass loading | HA in Rxn (% m/m) | Measured HA (% m/m) | stdev (%m/m) | n |
|---|---|---|---|---|
| Fn-HA$_{2000k}$ | 66 | 61.1 | ±2.9 | 11 |
| Fn-HA$_{15k}$ | 66 | 67.5 | ±2.1 | 9 |

| Re-growth kinetics | Max growth rate [%conf. / d] | t, 5% [d] | t, 50% [d] | t, 95% [d] |
|---|---|---|---|---|
| 2D CTFR Low | 10.9 | 3.1 | 9.3 | 14.5 |
| Fn CTFR Low | 10.0 | 3.7 | 11.5 | 19.1 |
| Fn-HA2000k CTFR Low | 8.6 | 4.8 | 13.1 | 21.5 |
| Fn-HA15 CTFR Low | 10.1 | 4.2 | 11.0 | 17.2 |

| Re-growth kinetics | Max growth rate [%conf. / d] | t, 5% [d] | t, 50% [d] | t, 95% [d] |
|---|---|---|---|---|
| Fn CTFR(+) | 7.7 | 8.4 | 18.2 | 26.5** |
| Fn-HA2000k CTFR(+) | 0.6 | 12.7 | i.d. | i.d. |
| Fn-HA15 CTFR(+) | 7.2 | 8.8 | 19.2 | 28.7** |

| Scratch Wound Kinetics | Closure rate [% wound / h] | StdErr Slope |
|---|---|---|
| 2D | 4.47 | 0.11 |
| Fn | 7.64 | 0.20 |
| $Fn\text{-}HA_{2000k}$ | 4.52 | 0.05 |
| $Fn\text{-}HA_{15k}$ | 5.53 | 0.13 |

ENGINEERED FIBRILLAR EXTRACELLULAR MATRIX NETWORKS FOR THREE-DIMENSIONAL (3D) CELLULAR SUPPORT SYSTEMS

CROSS-REFERENCE TO RELATED APPLICATIONS

This application claims the benefit of U.S. Provisional Application No. 63/339,335, filed May 6, 2022. The entire disclosure of the above application is incorporated herein by reference.

FIELD

The present disclosure relates to synthetic cellular support systems in the form of engineered extracellular matrices that may include a three-dimensional scaffold structure and at least one suspended fibril comprising an extracellular matrix protein, like fibronectin, and a glycan, like hyaluronic acid, spanning across a void in the three dimensional scaffold structure. These engineering fibrillary extracellular matrix networks are used for three-dimensional cellular support systems.

BACKGROUND

This section provides background information related to the present disclosure which is not necessarily prior art.

The extracellular matrix (ECM) is an astonishingly complex web of macromolecules that act on one another in reciprocity with cells to govern tissue development. ECM-focused efforts often fixate on the proteome (proteins) with rising attention given to the glycome (glycans), yet in tissue these disparate molecules interweave making their biological function inextricably bound. Two ECM components at the foundation of vertebrate biology are fibronectin (Fn) and hyaluronan (HA, also "hyaluronic acid" or "hyaluronate"). Fn is essential for life critically demarcating vertebrate biology and HA synthase 2 (HAS2) expression is critical in developing embryos. Both have complex roles in embryonic development, wound healing, and fibrotic remodeling in cancer progression. For example, accumulation of excess HA and Fn in tumors is associated with poor patient prognosis in breast cancer.

Despite reviews that indicate substantial knowledge regarding hyaluronan (HA) and its influence on tumor progression, hallmarks of tumor cell behavior that govern metastasis and recurrence are underexplored in the context of extracellular matrix (ECM) mediated regulation of tumor cells. Given the complex nature of native HA synthesis/degradation, concatenation to other signaling networks, and the difficulty in characterizing hyaluronan, cell-based models make it challenging to isolate the role of HA in tumor tissue. Additionally, biomaterial-based approaches to study tumor-associated HA utilize hydrogels that are not physiologically representative of tissue morphology, dimensionality, and ECM complexity. Hence, whether the overexpression and deposition of hyaluronan into tissues is itself a regulator of tumor cell fate or just a by-product of aberrant metabolism is an outstanding ambiguity. To address this, it would be desirable to be able to produce native-like engineered three-dimensional extracellular matrices (ECMs). Thus, it would be desirable to have a cellular support scaffold system that includes one or more biocompatible materials and a suspended networks of fibrils including at least one extracellular matrix protein, such as fibronectin, and at least one glycan, such as hyaluronic acid, that facilitates robust cell growth and proliferation in three-dimensions, while providing control over composition and morphology.

DRAWINGS

The drawings described herein are for illustrative purposes only of selected embodiments and not all possible implementations, and are not intended to limit the scope of the present disclosure.

FIGS. 1A-1F. Defined derivatization of HA enables minimally modified thiol reactive species. A: thiol-reactive functionalization of hyaluronic acid. B: 1H NMR spectrum of 40% degree of substitution modification of 15 kDa HA confirming successful chemical modification. C: SEC-MALS (620 nm laser) demonstrating that molecular weight is not affected by modification strategy. D: illustration depicting site-specific thiol conjugation strategy to produce HA-Fn conjugates that produce fibrillar EECMs via hydrodynamically induced fibrillogenesis. E: Merged CLSM MIP of Fn-HA EECM (15 kDa HA) where Fn is depicted in green and HA is depicted in magenta. Contrast and gamma adjustments were applied for display purposes F: SEMs of of Fn EECMs vs Fn-HA EECMs demonstrating fibrillar morphology at higher resolution.

Figure 2:
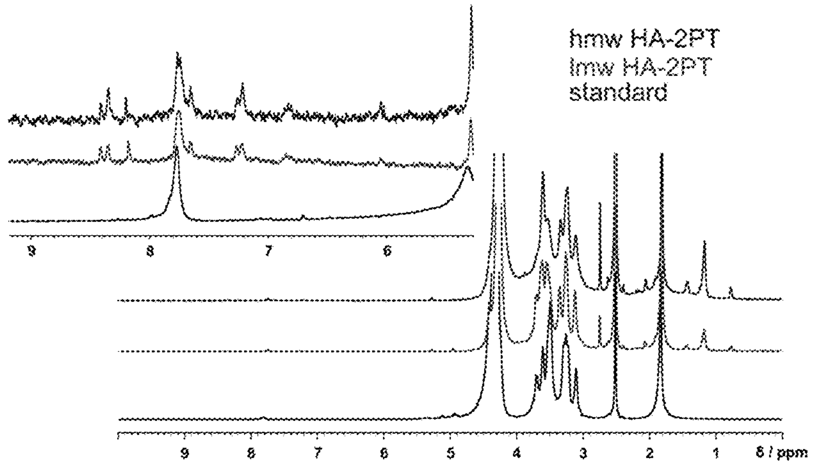

FIG. 2. H NMR spectrum of 14% degree of substitution modification of 2000 kDa HA (hmw HA-2PT) and 15 kDa (lmw HA-2PT).

FIGS. 3A-3E. Fn EECMs assemble according to biomimetic hallmarks enabling a site-specific HA-conjugation strategy A: CLSM MIPs of nFn EECMs stained for EDA-Fn (yellow), non-specific Fn (green) compared to an isotype control. Quantification was performed using a platereader for the EDA-Fn stain (Ex: 490 nm, Em: 530 nm).B: brightfield image of nFn hydrodynamic coating that were treated with 70 kDa fragment (top) or with nothing (bottom)C: CLSM MIPs of Dylight-488 conjugated nFn that has been untreated (left) or treated with 20 mM reducing agent TCEP (right). Quantification of total coverage was performed on CLSM MIPs and shows dramatic reduction of area coverage for nFn treated with TCEP. D: Image of SDS PAGE gel comparing Fn in tris vs borate buffer, HA-Fn conjugates following thiol specific strategy, nFn treated with 20 mM TCEP and Fn treated with beta mercaptoethanol (β-ME). E: CLSM MIPs of HABP stained (magenta) EECMs after incubation at 37 C for 5 d in DPBS comparing different conjugation strategies. +Unfold (+Un) indicates unfolded nFn. "R-HA" denotes modified, thiol reactive HA compared to native HA. 2000 kDa HA was used in these studies. Fn EECM were Fn EECMs without any HA treatment used as a negative control. Quantification was performed on MIPs (far right). $*P \leq 0.05$, $P \leq 0.01$, $*P \leq 0.001$.

FIGS. 4A-4D. Evaluation of various nFn products. A: Area coverage analysis based on CLSM MIPs assessed either from from general Fn pAb staining (left) or EDA-Fn specific mAb staining (right). B: brightfield image of TPSs that were hydrodynamically coated with Fn from different vendors. C: Ratiometric platereader analysis of signal from EDA-Fn normalized by general Fn stain. D: SDS-PAGE of Fn products from different vendors to assess the presence of dimeric protein content in the unreduced state vs Sigma Fn treated with β-ME (far left lane).

FIGS. 5A-5D. A: CLSM MIPs and analysis from FIG. 3, with additional group where Fn EECMs were treated with soluble native HA2000 kDa for the duration of the study (5 d) as well as additional unbiased quantification methods using a platereader to validate image quantification. CLSM MIPs of HABP stained EECMs comparing different conjugation strategies (top row). DIC counter images (bottom row) are provided to demonstrate fibrillar EECM was present in each condition. +Unfold (+Un) indicates unfolded nFn. "R-HA" denotes modified, thiol reactive HA compared to native HA. 2000 kDa HA was used in these studies. Fn EECM were Fn EECMs without any HA treatment used as a negative control. B: is the same integrated density quantification as FIG. 3 where Fn EECMs were used to determine the pixel intensity threshold cutoff for analysis. C: Orthogonal quantification using a platereader, assessing just the HABP stain (Ex 490 nm/Em 530 nm). D: Platereader analysis where EECMs were co-stained with pAb for Fn and HABP/pFn ratios were normalized to nFn +Un +R-HA2000 kDa *P≤0.05, P≤0.01, *P≤0.001 ****P≤0.0001.

FIGS. 6A-6E. Characterization of Fn-HA EECMs of different molecular weights compared to Fn EECMs. A: CLSM MIP of Fn-HA EECMs (Fn-15 kDa top row, Fn-2000 kDa bottom row) where Fn and HA were visualized with fluorescent tags (Dylight 488 and Cy5, respectively). B: Manual fibril diameter analysis of Fn-HA conjugate EECMs compared to pure Fn EECMs. Each group is represented by split histogram, violin plot and box-whisker. C: High resolution 3D volume renders comparing Fn-HA conjugates with different molecular weights. D: Summary of mass loading quantification (top) and fibril diameter analysis (bottom). E: Platereader quantification of EECMs where HABP/aFn pAb ratios were normalized to Fn-HA2000 kDa EECMs. *P≤0.05, P≤0.01, *P≤0.001 ****P≤0.0001.

Figures 6A, 6B, 6C, 6D, 6E:
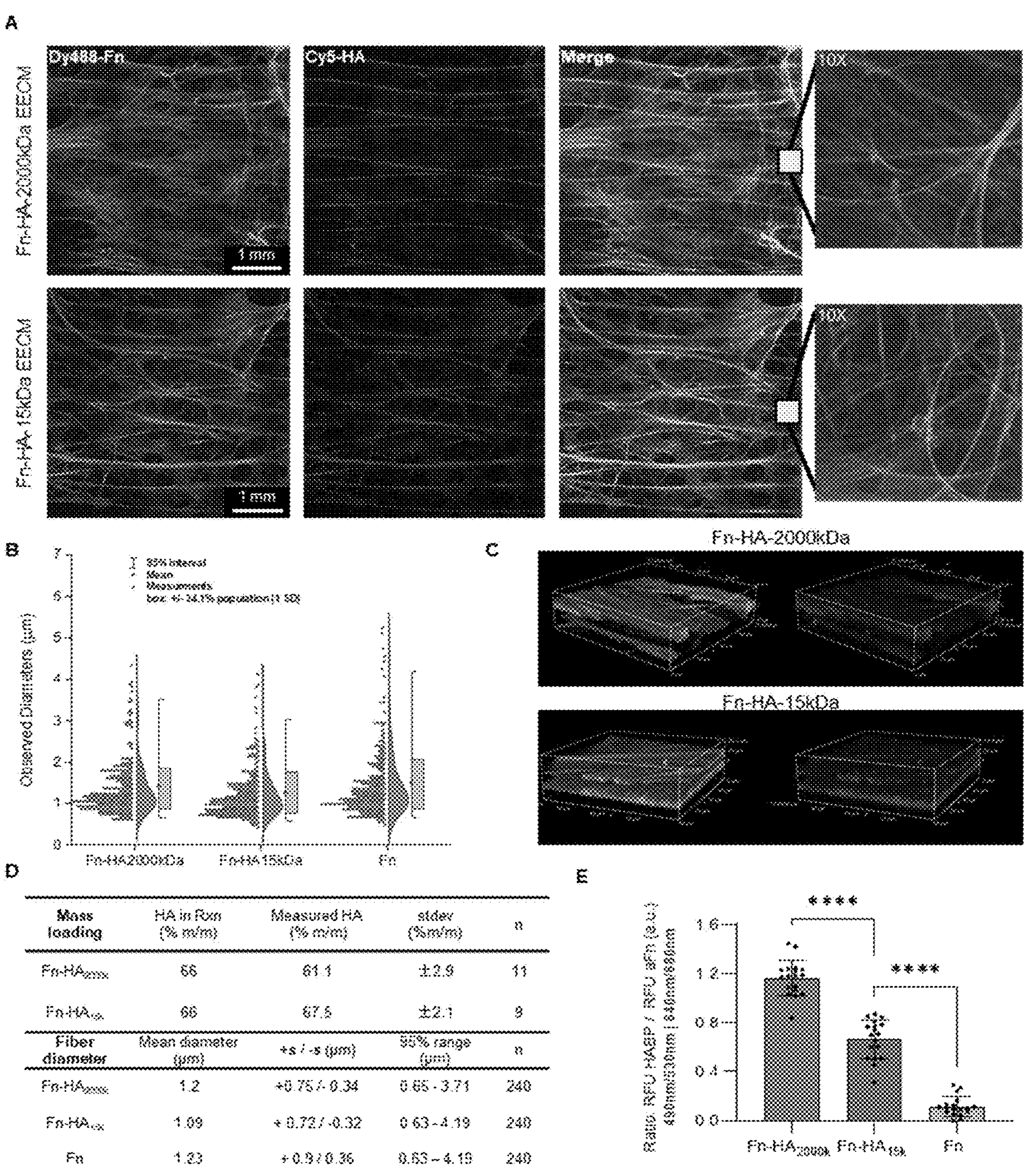
Figure 7A:
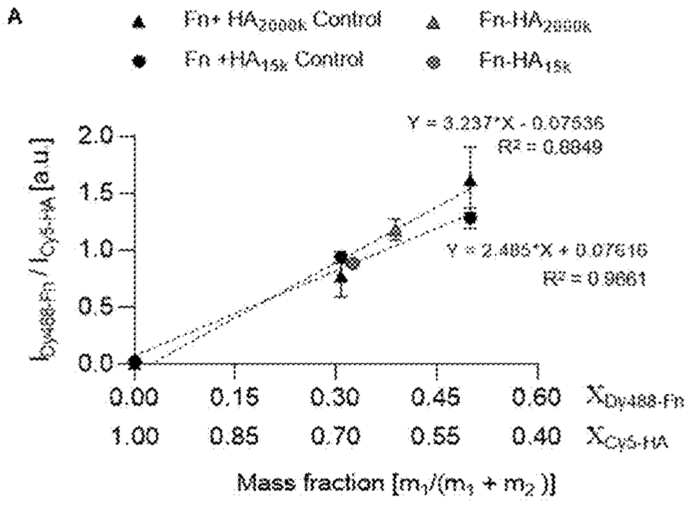
Figure 7B:
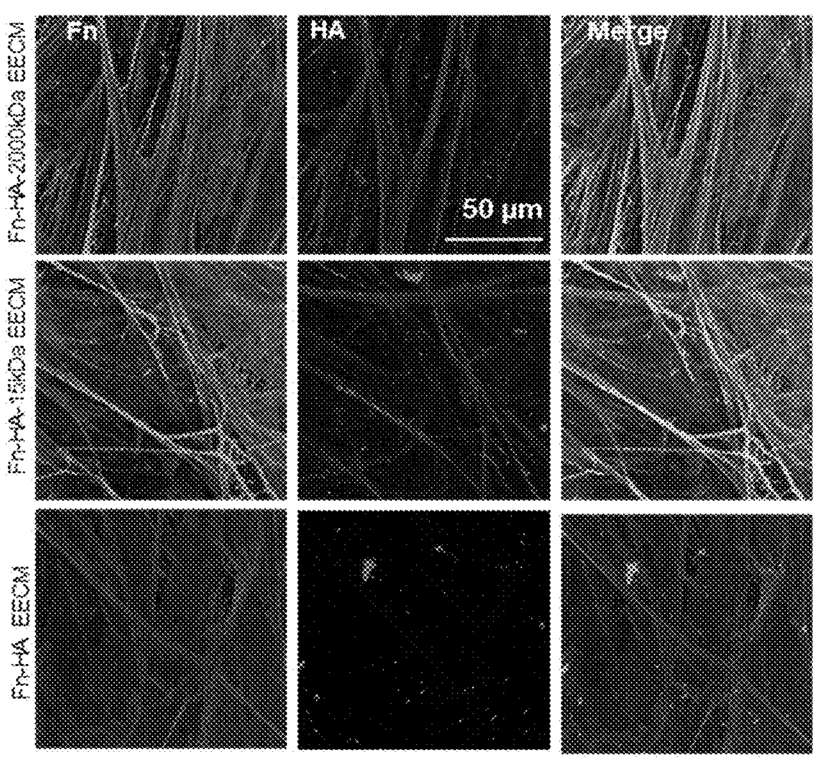

FIGS. 7A-7B. A: linear regressions of sample Fn-HA15 kDa and Fn-HA2000 kDa EECMs compared to respective 3D gelatin controls with known mass loading used to determine mass ratios of HA in Fn fibrils within EECms. B: CLSM MIPs of EECMs stained with aFn pAb (green) and HABP (magenta). These EECMs were used in the platereader quantification from FIG. 6E.

Figures 8A, 8B:
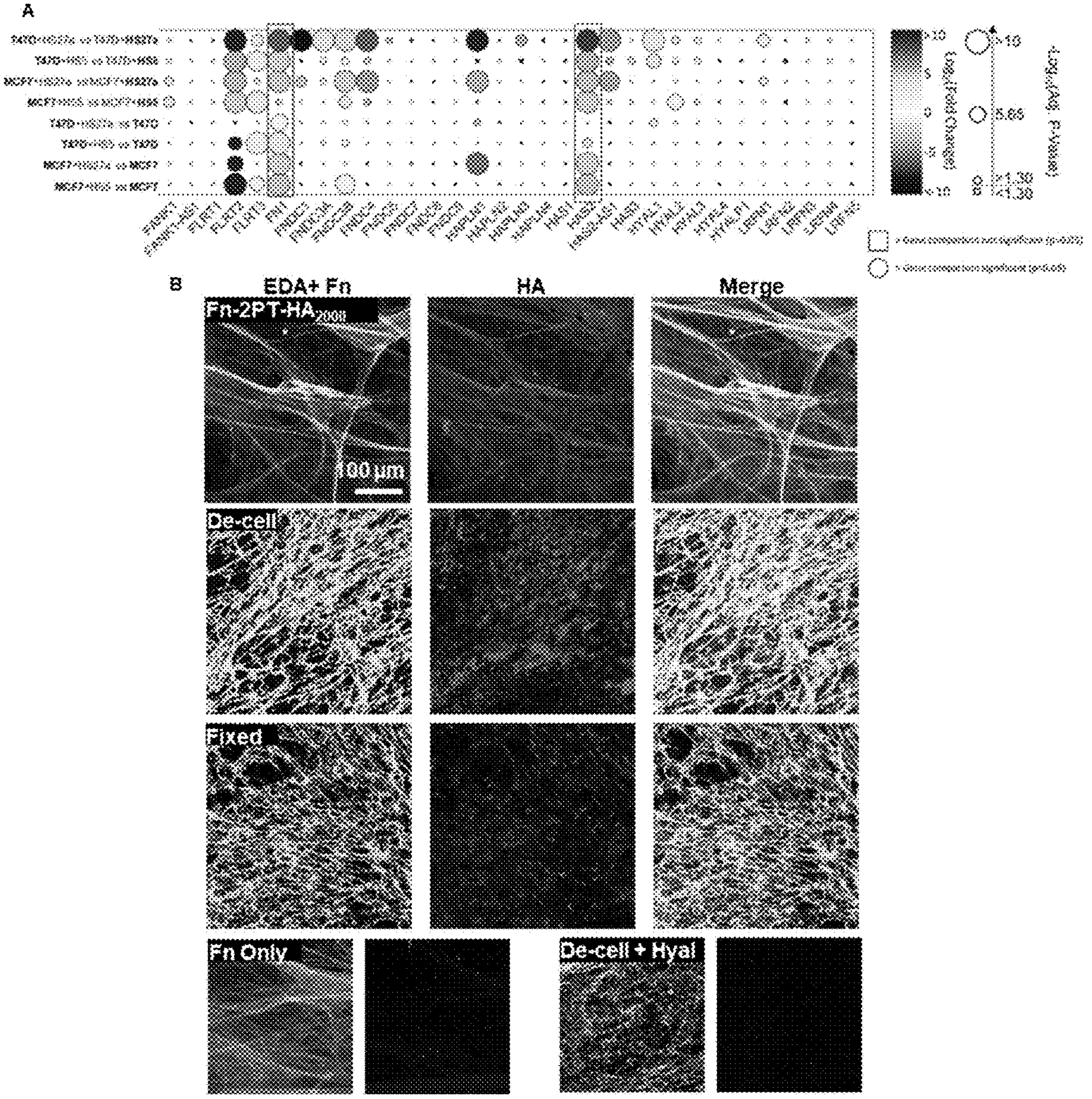

FIGS. 8A-8B. Fn-HA EECMs display tumor-mimetic morphology and biochemistry A: Bulk RNA-seq analysis of breast cancer cell lines (T47D, MCF7) co-cultured with two bone marrow stromal cell lines (HS27a, HS5). Co-cultured breast cancer cells (bold) were compared to stromal cells (bold) in the top 4 rows. Where breast cancer cells co-cultured (bold) were compared to standard monocultured breast cancer cells (bold) in the bottom 4 rows. B: CLSM MIPs of Fn-HA2000 kDa EECM stained with EDA-Fn (yellow) co-stained with HABP (magenta) in the top row compared to MCF7/HS5 co-cultures subjected to de-cellularization (2nd row), fixed MCF7/HS5 co-cultures (3rd row) with imaging controls of Fn only EECMs and de-cellularized co-cultures treated with hyaluronidase in the bottom row.

FIGS. 9A-9J. MCF7 cells grown on Fn-HA EECMs, Fn EECMs and TCPS (2D) in 2% (v/v) FBS were characterized to assess phenotype and epithelial/mesenchymal tumorigenic characteristics. A: representative brightfield images of MCF7s on different conditions after 6 d before being assayed in all other panels. B: viability assessed by flow cytometry for DAPI negative MCF7s. C: Spheroid formation assay in methyl cellulose containing MEBM assessed after 15 d in sphere culture. D: Scratch wound assay following 4.5 d of regrowth with linear regressions (solid colored lines) with error for fits (corresponding dotted lines). E: Dye retention assay using CTFR dye to quantify non-proliferating cells denoted CTFR+ with flow cytometry. F: Phenotyping by flow cytometry to quantify populations of CD44+/− and CD24+/− cells. G: Phenotyping by flow cytometry to quantify dual positive ALDH+/CD44+ 24− BCSCs. H: Phenotyping by flow cytometry to quantify CD44+ 24− that are in the CTFR+ subpopulation. I: Regrowth curves of MCF7s that were CTFR+ or CTFR low that were replated into 96 well TCPS plates growth in full, 10% FBS medium where regrowth kinetics were are summarized in J. Values with ** here indicate fitted values reported outside of time course and i.d. represents insufficient data for fitted values during the time course assessed. *P≤0.05, P≤0.01, *P≤0.001 ****P≤0.0001.

FIGS. 10A-10D. D2.OR cells grown on Fn-HA EECMs, Fn EECMs and TCPS (2D) in 2% (v/v) FBS were characterized to assess epithelial/mesenchymal tumorigenic characteristics. B,C: also include D2.ORs grown in full serum (10% FBS), TCPS coated with Fn or Fn-HA conjugates (2D+ groups), as well as D2.ORs grown in non-methyl cellulose containing MEBM (suspension). A: representative brightfield images of D2.OR on different conditions after 5 d before being assayed in all other studies with D2.ORs. B: viability assessed by flow cytometry for DAPI negative D2.OR cells. C: Spheroid formation assay in methyl cellulose containing MEBM assessed after 15 d of sphere culture. D: Scratch wound assay following 3 d of regrowth with linear regressions (solid colored lines) with error for fits (corresponding dotted lines). *P≤0.05.

FIGS. 11A-11F. D2.OR cells grown on Fn-HA EECMs, Fn EECMs and TCPS (2D), TCPS coated with Fn or Fn-HA conjugates (2D+ groups), in 2% (v/v) FBS compared with cells grown in full serum (2D 10% FBS), and non-methyl cellulose containing MEBM suspension culture to assess conditions that promote CTFR+ populations. A: Illustration of experimental work flow. B: CTFR+ cells assessed by flow cytometry. C: Spheroid formation assay in methyl cellulose containing MEBM assessed after 15 d of sphere culture for CTFR+ cells compared to CTFR low cells. D: Representative histograms of CTFR+ or low cells to show relative population distributions as a function of culture substrate. E: CTFR+ cells from mammosphere culture that were filtered and replated on TCPS in 10% FBS. F: Representative brightfield images of regrowth assay in E. *P≤0.05, P≤0.01, *P≤0.001 ****P≤0.0001.

FIGS. 12A-12F. D2.OR cells grown on Fn-HA EECMs, Fn EECMs and TCPS (2D), in 2% (v/v) FBS for 5 d injected into NODscid mice to assess in vivo tumor growth and overall survival. A: Illustration of experimental work flow B: Comprehensive imaging of all mice in the study. Some mice do not appear in later images because they excluded due to procedure-related death. C: In vivo growth dynamics over the first 50 d. D: Doubling time (d) for growth dynamics assessed via non-linear of log 10 from C. E: Number of mice excluded from each group because they died due to surgical procedures. F: Survival curve where at this point in the study, no mice have died due to tumor burden.

Corresponding reference numerals indicate corresponding parts throughout the several views of the drawings.

DETAILED DESCRIPTION

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "engaged to," "connected to," or "coupled to" another element or layer, it may be directly on, engaged, connected or coupled to the other component, element, or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first," "second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Spatially or temporally relative terms, such as "before," "after," "inner," "outer," "beneath," "below," "lower," "above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. For example, "about" may comprise a variation of less than or equal to 5%, optionally less than or equal to 4%, optionally less than or equal to 3%, optionally less than or equal to 2%, optionally less than or equal to 1%, optionally less than or equal to 0.5%, and in certain aspects, optionally less than or equal to 0.1%.

In addition, disclosure of ranges includes disclosure of all values and further divided ranges within the entire range, including endpoints and sub-ranges given for the ranges.

Example embodiments will now be described more fully with reference to the accompanying drawings.

In various aspects, the present disclosure contemplates a cellular support system. The cellular support system may comprise a three-dimensional scaffold structure comprising at least one void. It may further comprise at least one suspended fibril spanning across the at least one void in the three-dimensional scaffold structure. In certain aspects, a plurality of distinct fibrils spanning across the at least one void in the three-dimensional scaffold structure to define a fibrillar network in the at least one void. As will be described further herein, the suspended fibril comprises at least one extracellular matrix protein and at least one glycan. The glycan may be associated or conjugated with the extracellular matrix protein within the fibril, for example, associating via weak forces or bonded together (referred to herein as "decorating" the extracellular matrix protein with a glycan). For example, in certain variations, a controlled disulfide conjugation strategy occurs at fibronectin (FnIII) with minimally modified (e.g., thiol functionalized) hyaluronic acid (HA). In certain aspects, fibronectin fibril assembly can be induced with hydrodynamic fibrillogenesis that is not believed to be reliant on domain interactions or disulfide bonds involving FnIII. In this manner, the at least one suspended fibril is formed that is capable of supporting cells and promoting three-dimensional cellular growth.

By "promoting" cell growth, cell proliferation, cell differentiation, cell repair, or cell regeneration, it is meant that a detectable increase occurs in either a rate or a measurable outcome of such processes when the cellular support system is present as compared to a cell or organism's process in the absence of the cellular support system, for example, conducting such processes naturally. By way of example, as appreciated by those of skill in the art promoting cell growth in the cellular support system may increase a growth rate of target cells or increase a total cell count of the target cells, when compared to cell growth or cell count of the target cells in the absence of such a cellular support system. By "supporting" cell growth, cell proliferation, cell differentiation, cell repair, or cell regeneration, it is meant that the cellular support system provides a physical substrate for one or more target cells that enhances target cell growth, vitality, proliferation, differentiation, repair, or regeneration, by way of non-limiting example. As appreciated by those of skill in the art, the cellular support system may both support and promote the growth, vitality, proliferation, differentiation, repair, and/or regeneration processes of one or more target cells in vitro, ex vivo, or in vivo, for example. The cellular support system thus can serve a role as a cellular scaffold structure that supports and/or promotes target cell growth, target cell proliferation, target cell differentiation, target cell repair, and/or target cell regeneration in three-dimensions, in contrast to the support and growth on conventional two-dimensional planar or two-dimensional scaffold surfaces. The cellular support system of the present disclosure can be employed to promote growth of one or more target cells in a predetermined three-dimensional pattern.

The suspended fibril can provide cells with an ECM-like network of protein and glycan, which may be remodeled by the cells, allowing for study of cell migration and metastasis. When cells secrete insoluble proteins to form their microenvironment, they are also revealing biologically active cryptic binding sites on the protein that are otherwise inaccessible to cells when the protein is solubilized. Here, because the extracellular matrix proteins, like fibronectin, present in the protein fibrils are insoluble, the cryptic binding sites can be revealed despite being fully-defined and cell-free.

An extracellular matrix protein is one or more of the large structural fibrillar proteins often found physiologically in the extracellular matrix (ECM) of animals or plants. In certain aspects, the at least one extracellular matrix protein comprises fibronectin.

The suspended fibril may further comprise one or more proteins selected from the group consisting of: collagens, laminins, tenascins, elastin, vitronectin, periostin, and combinations thereof. In certain variations, the suspended fibril further comprise collagen, such as Type I collagen.

The at least one glycan may comprise a glycosaminoglycan. In certain variations, the glycosaminoglycan comprises hyaluronic acid (HA). HA is a linear, non-sulfated, negatively charged glycosaminoglycan synthesized at the surface of cells whose extracellular presentation is controlled by transmembrane synthesis enzymes (HAS1, HAS2, and HAS3) and six known degradation enzymes (hyaluronidases). In certain aspects, the hyaluronic acid has a molecular weight of greater than or equal to about 15 kDa to less than or equal to about 15,000 kDa. It may be functionalized, for example, with a thiol-reactive group prior to forming the fibrillary network on the three-dimensional support, as will be described further below.

In certain variations, a mass ratio of the at least one extracellular matrix protein to the at least one glycan is greater than or equal to about 1:1 to less than or equal to about 1:3, optionally greater than or equal to about 1:1.5 to less than or equal to about 1:2.5, and in certain particular variations, about 1:2.

Each suspended fibril in the network may have an average diameter of greater than or equal to about 1 micrometer to less than or equal to about 1.5 micrometers. In certain variations, the suspended fibril has a millimeter scale length, for example, having a length of greater than or equal to about 1 mm.

The three-dimensional scaffold structure may have a void with a major dimension of greater than or equal to about 0.1 micrometers to less than or equal to about 5 centimeters. The three-dimensional scaffold structure is optionally formed from a material selected from the group consisting of: a metal material, a polymeric material, a composite material, a ceramic material, a biologically-derived material, and combinations thereof. In one variation, the three-dimensional scaffold structure comprises a polymer and is formed from a polymeric precursor or is a polymer selected from the group consisting of: polylactic acid, polyglycolide, polycaprolactone, poly(lactide-co-glycolide), poly(lactide-co-caprolactone), polyethylene glycol, starches, polydimethylsiloxane, polyurethanes, polyolefins, polyamides, celluloses, lignins, biodegradable polyesters, polystyrene, and combinations thereof.

In certain particular variations, the present disclosure contemplates a cellular support system that comprises a three-dimensional scaffold structure comprising at least one void and a fibrillar network comprising a plurality of suspended fibrils spanning across the at least one void in the three-dimensional scaffold structure. Each of the suspended fibrils comprises fibronectin and hyaluronic acid. In certain aspects, the fibrils may further comprise one or more proteins selected from the group consisting of: collagens, laminins, tenascins, elastin, vitronectin, periostin, and combinations thereof. In certain variations, the fibrils further comprise another protein, such as collagen. The fibrillar network is capable of supporting cells and promoting three-dimensional cellular growth. The hyaluronic acid may have a molecular weight of greater than or equal to about 15 kDa to less than or equal to about 15,000 kDa. In certain variations, a mass ratio of the fibronectin to the hyaluronic acid in the fibrils is greater than or equal to about 1:1 to less than or equal to about 1:3, optionally greater than or equal to about 1:1.5 to less than or equal to about 1:2.5, and in certain variations, about 1:2.

Each of the suspended fibrils has an average diameter of greater than or equal to about 1 micrometer to less than or equal to about 1.5 micrometers and a length of greater than or equal to about 1 mm.

The three-dimensional scaffold support may be any of those described above.

By way of further background, the inventive technology is described in further detail herein. The cellular support systems contemplated by the present disclosure take advantage of certain ECM proteins and glycans, like HA and Fn, leveraging their stability, assembly, and biochemistry to produce native-like engineered ECMs. This methodology leads to remarkable control over EECM fibrillar topography and HA mass ratio. Fn-HA EECMs further display morphological and biochemical similarity to a cell-derived tumor associated system. Then Fn EECMs decorated with high (2,000 kDa) and low molecular weight (15 kDa) HA-Fn EECMs were employed to study the effect HA accumulation and degradation in primary tumor tissues has on epigenetically regulating the metastatic potential of breast tumor cells.

As noted above, HA is a linear, non-sulfated, negatively charged glycosaminoglycan synthesized at the surface of cells whose extracellular presentation is controlled by transmembrane synthesis enzymes (HAS1, HAS2, and HAS3) and six known degradation enzymes (hyaluronidases). Critical to its biological role, HA presents in fluids, acts as a lubricious water-laden semisolid in connective tissue and is heavily implicated in tumor progression in various tissue-types. HA's incorporation into tissue niches like cartilage is relatively well defined and proteoglycan-HA cable structures are identified as immune cell modulators, but HA's many-faced roles in the tumor microenvironment remains unclear.

Qualitatively, "high" molecular weight is described as "healthy," whereas "low" molecular weight or "fragmented" HA is "diseased/inflamed," yet there are many caveats and exceptions to this assertion. For instance, naked mole rats, whose cultured cells secrete ultrahigh molecular weight HA (6,000 kDa-12,000 kDa HA) are peculiarly resistant to developing cancer with unusually long lifespans. Comparatively, approximately 300 kDa up to 2,000 kDa is generally regarded as the high-end of HA molecular mass with other reports up to 6,000 kDa in human physiology. Despite conflicting reports, certainly these large polymeric HA molecules are simultaneously degraded in solution and tissues leading to fragments. Soluble fragmented oligomeric HA has been shown to promote angiogenesis and stimulate matrix metalloproteases (critical for tumor progression), yet delivery to tumor xenografts inhibited tumor growth. It has been previously demonstrated oligomeric HAs inhibited angiogenesis in a CD44/CXCR4/CXCL12 dependent manner. In colorectal cancer patients, most HA analyzed in tumor tissue fluids was of higher molecular weight, but oligomeric HA of 6-25 disaccharides (about 2.4 k-10 k) was detected in a subset of tumors that was not present in healthy tissues and correlated with lymph node invasion/metastases. While soluble HA is well studied, the role of tissue bound HA is more elusive.

In an insoluble state, HA forms a robust pericellular coating and accumulates significantly in remodeled, fibrillar tumor tissue. Overexpressing hyaluronidase to combat this and may inhibit growth in breast and colon cancer but stimulated metastasis in prostate cancer. Clinical approaches to deliver hyaluronidases may be helpful in improving the delivery of adjuvant therapies, but their clinical adoption is limited by unclear in vivo mechanisms and concerning toxicity profiles. Interestingly, expression of HAS2, thought to encode for high Mw HA, is heavily implicated in invasive/metastatic breast cancer and oligomers of 3-9 disaccharide units (approximately 1.8 kDa-3.5 kDa) can outcompete polymeric HA binding attenuating signaling to prevent tumorigenic outcomes.

CD44, a cell membrane protein and HA-binding protein (HABP) is heavily implicated in cancer progression as is used as a marker for highly tumorigenic, stem-like cancer cells. CD44 has served as a target for direct disruption HA binding with concerning efficacy and side effects. Recently, soluble HA was implicated as a carrier of iron via CD44-mediated endocytosis preserving epithelial to mesenchymal transitioned (EMT)/cancer stem cell (CSC) phenotypes. Therefore, conflictingly, higher molecular weight HA-tumor cell binding seems to be implicated as a necessary component of tumorigenesis with outstanding postulates about whether high molecular weight-HA prevents invasive/EMT-phenotypes or enhances EMT, migration and invasion. Lengths of tissue bound HA that promote differential tumor cell phenotype are underexplored creating a dire need for engineered systems to faithfully recapitulate tumor-ECM heterogeneity to dissect the complexities of HA in tumor stroma.

Fibronectin (Fn) expression is commonly used as a marker for EMT and has been implicated in promoting stemness and metastatic spread in breast cancer cells. To directly probe whether stromal bound HA would enhance or perturb invasive/metastatic phenotypes in a Mw dependent manner, minimally modified HA is conjugated to native Fn (nFn) isolated from blood plasma to engineer three-dimensional (3D) tumor-mimetic tissue scaffolds. These engineered extracellular matrices present with native morphology, biochemistry and afford well controlled physical properties. Remarkably, after only 5-6 days of culture on Fn-HA EECMs, EECMs impart lasting phenotypic changes that are correlated with metastasis and recurrence. While not limiting, this is believed to constitute the first report assessing the co-operative role of Fn and HA in stromal tissue as an epigenetic regulator of tumor metastasis using a well-defined engineered system with native materials.

Defined Derivatization of HA Enables Minimally Modified Thiol Reactive Species

Hyaluronic acid's simple linear structure is made up of disaccharide repeat units of linked D-glucuronic acid and N-acetyl-D-glucosamine (GlcNAc), FIG. 1A. As a result, its biological role is largely influenced by differential molecular weight defining physical properties and binding mechanisms to other biomolecules and cell surfaces. HA is notoriously difficult to isolate, stabilize, and accurately characterize contributing to the discrepancies that mar the understanding of HA's biological role, especially in pathogenesis. Furthermore, complex bioregulation of HA synthesis and degradation makes using cell or tissue-based in vitro models intensely challenging to present HA in a controlled fashion. Engineered technologies therefore offer an attractive approach; however, HA is most commonly formed into hydrogels lacking tumor relevant fibrillar morphology and dimensionality. Other approaches include conjugation to proteinaceous materials using non-specific amide chemistry potentially leading to ambiguous modifications that likely impact HA-binding. Or simple steric intercalation methods are used to sequester HA in alginate gels. Pre-modification strategies of HA to make it reactive offers a measured path forward where quality control measures can be employed.

A thiol reactive strategy was employed with (S)-2-Pyridylthio cysteamine (2PT) used as the functional linker-moiety shown in FIG. 1A. 1H NMR spectra of highly modified (40% degree of substitution) versus unmodified HA show the methyl peak of the N acetyl moiety from the GlcNAc subunit at 1.9 ppm appears a sharp singlet for both (FIG. 1B). In contrast, the multiplets at 7.2-8.4 ppm indicate the attachment of the thio-pyridyl group confirming the modification strategy was successful. Size exclusion chromatography multi-angle laser light scattering (SEC-MALLS) was employed to obtain absolute measures of molecular weight, see FIG. 1C, according to a previously published method developed by Botha et al. For SEC of the modified and pure HA, the do/dc values were determined in a concentration range of 0.3-2.1 g/L (with 0.3 g/L increments). Compounds in DMSO/$H_2O$ mixture 6/4 (v/v) with 0.05 M LiBr was applied at an operating temperature of 40° C., where a RI detector was utilized with a flow rate of 0.3 mL/min. With the physical correlation between the intensity of the scattered light and the do/dc value for its concentration, the MW can be determined after an approximation for larger particles above the 10 nm range. SEC elution curves indicate similar distributions with approximately 20 min elution times and similar peak maxima, FIG. 1C. The data summarized in the adjacent table (FIG. 1C) confirm the expected nominal shifts in the weight average molecular weight (Mw approximately 17.3 kg/mol versus approximately 19.3 kg/mol) following chemical derivatization attributed to the addition of the reactive leaving group. The dispersity index (D) decreases for the 2PT modified group, likely due to purification following the reaction. It can be concluded that the synthesis approach was successful, and no polymer chain degradation or crosslinking/polymerization having occurred. HA of this length is herein referred to as "15 k" per the manufacturer's label. Given the promising characterization at higher degrees of substitution (40%, theoretical), a lower degree of substitution of 2PT modification (14%, theoretical) was chosen as HA-binding literature has been based on 8-mer HA (4 disaccharide subunits). This degree of substitution would preserve a total of approximately 33 disaccharide subunits per smaller HA molecule (15 k g/mol) statistically preserving many unmodified multi-unit blocks. 1H NMR confirmed successful modification of both "15 k" (15 k g/mol) and "2000 k" (2000 k g/mol) HA at lower degrees of substitution, FIG. 2. These lengths were chosen to model high molecular weight HA in tissue (2000 k), as well as the fragmented-tissue bound remains (15 k) to create 3D tissue scaffolds co-expressed with native Fn as a tumor-mimetic environment.

Native, dimeric Fn (nFn) has two free thiols per monomer buried conformationally in solution ("cryptic") at type-III domains 7 and 15 that can be leveraged for site-specific conjugation following unfolding of the protein. The protein can then be refolded following modification and used to initiate in vitro fibril assembly by drawing fibers or assembled by cells in culture, as Vogel and colleagues demonstrated. An approach adapted from these techniques was employed (illustrated in FIG. 1D) to promote Fn unfolding in 4 M guanidine hydrochloride (Gdn) in a slightly basic buffer (0.05 M sodium borate, pH 8.5) to promote cleaving of the N-heterocycle with the thiol-terminus of Fn's cysteine in $FnIII_7$ and $FnIII_{15}$ leading to di-sulfide linked Fn-HA conjugates. The conjugation mixtures were purified using dialysis. Hydrodynamic fibrillogenesis, previously published by our lab, was then employed to create 3D EECMs for cell culture. Shown in a CLSM MIP, FIG. 1E, these EECMs are able to cover multi-millimeter areas and have fibrillar morphology. SEMs display fibrillar morphology of Fn and Fn-HA EECMs at higher resolution, FIG. 1F. Additional characterization is presented in the following sections.

Figures 3A, 3B, 3C, 3D, 3E:
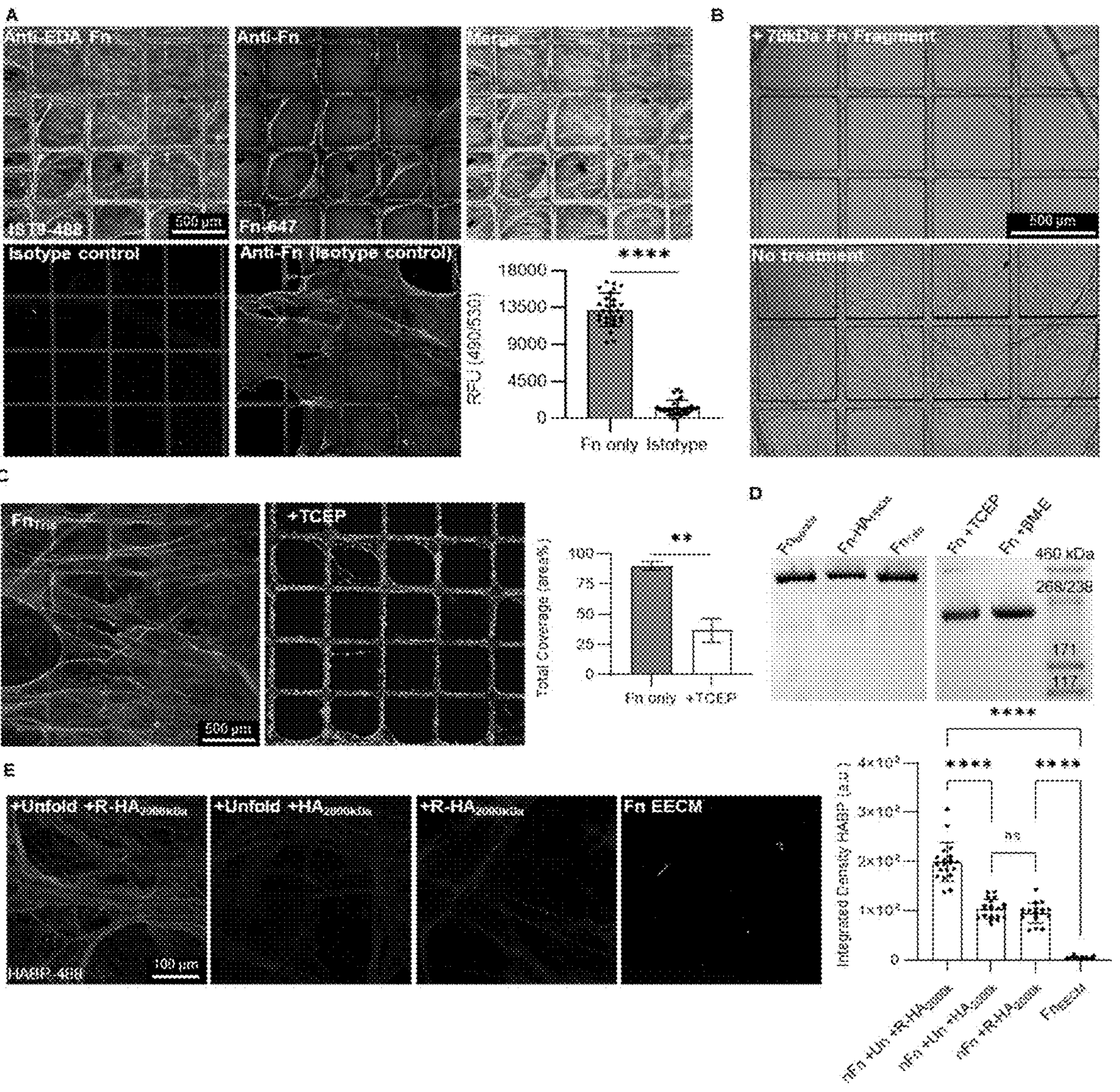
Figures 4A, 4B, 4C, 4D:
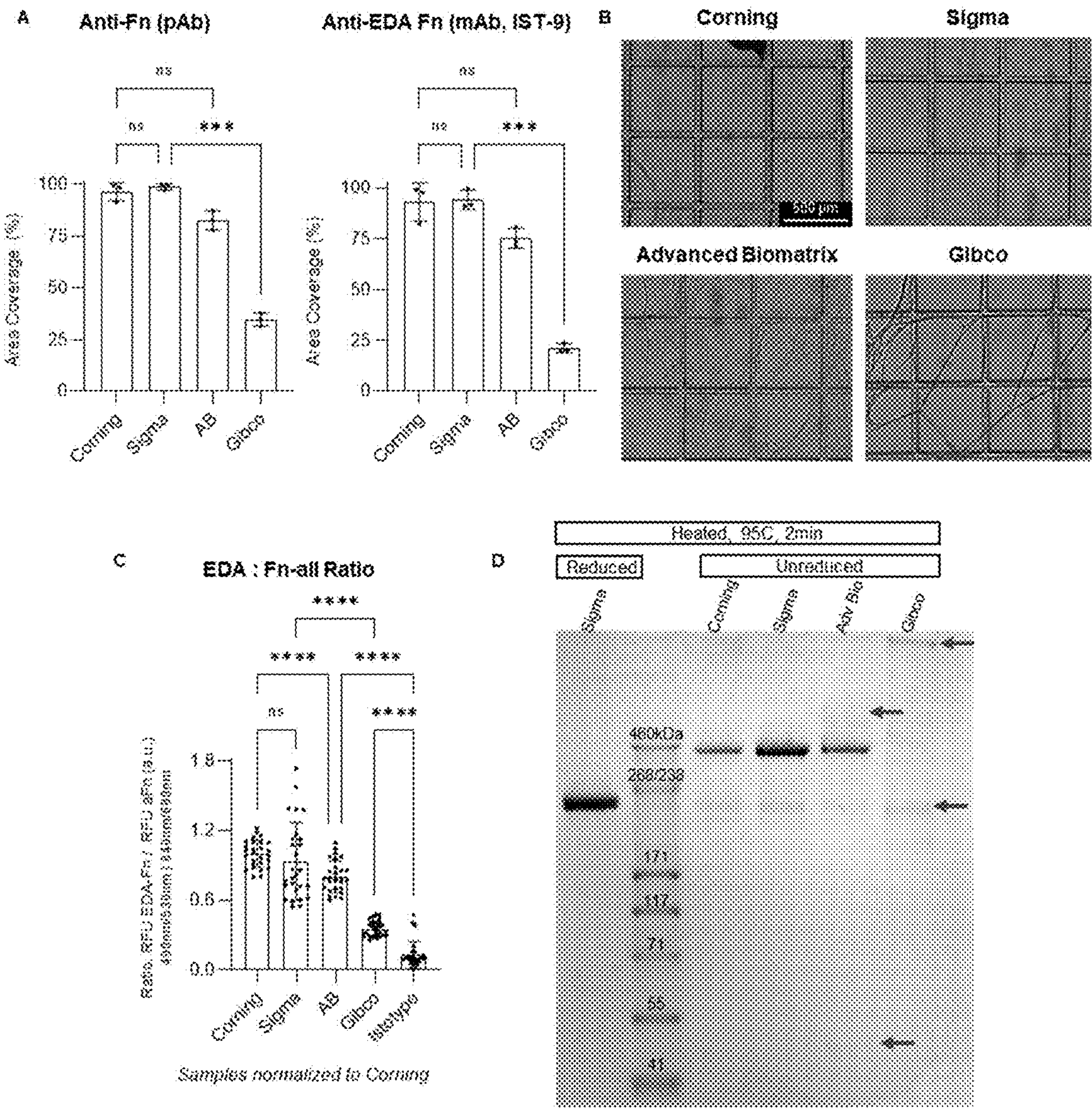
Figures 5A, 5B, 5C, 5D:
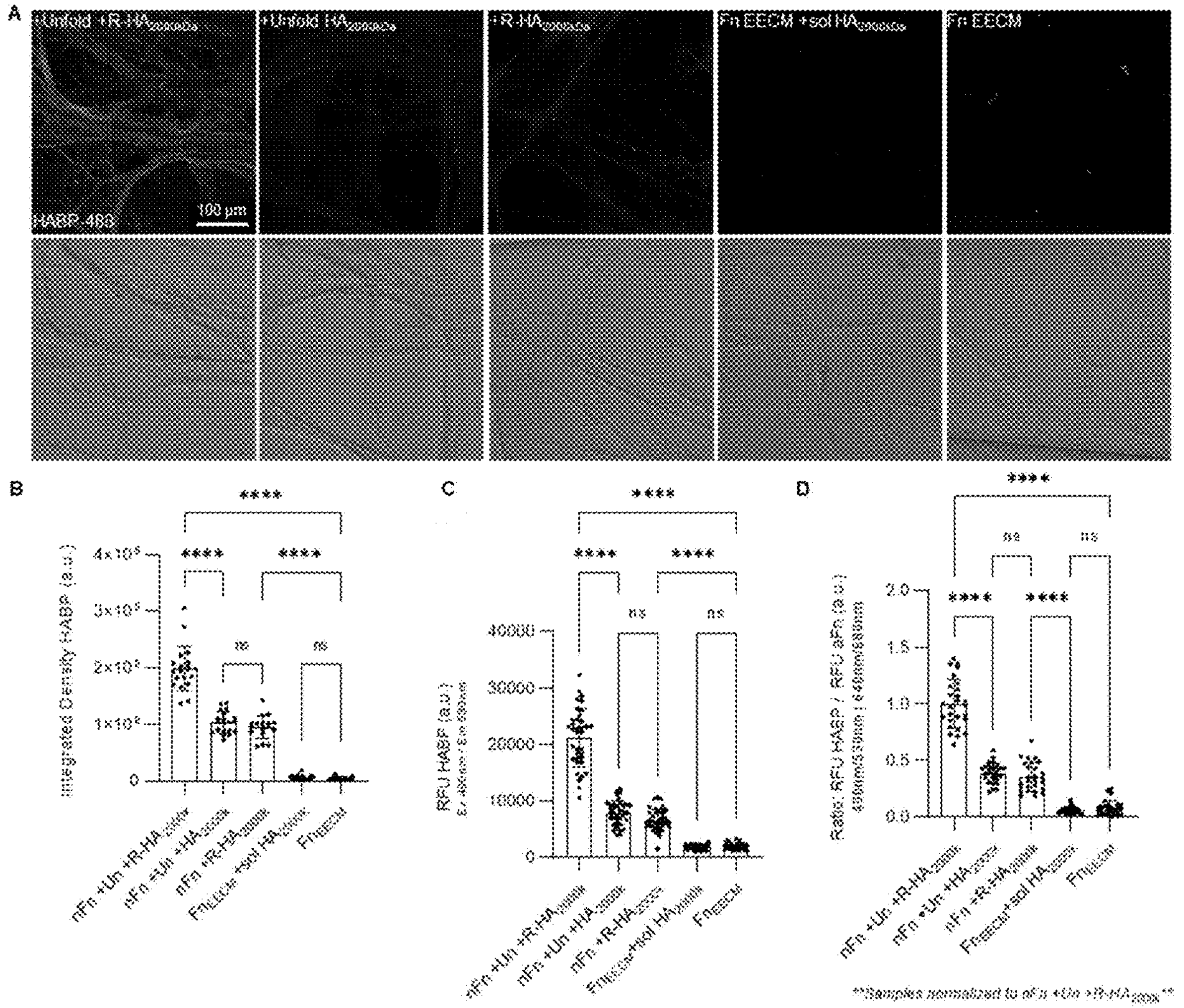

Fn EECMs Assemble According to Biomimetic Hallmarks Enabling a Site-Specific HA-Conjugation Strategy Fn is a mechanosensitive protein with conformationally active domains whose ECM assembly is dependent on dimeric protein unfolding inducing intermolecular binding that produces insoluble multimeric fibrillar structures. While not limiting to any particular theory, in vitro processes are thought to leverage this native phenomena to produce assembled-Fn biomaterials, overviewed elsewhere. Among the many bio-active Fn domains, the cellular fibronectin splice variant containing the extracellular domain A (EDA or EIIIA) has been implicated in sustaining CD44+ colon cancer cells, and breast cancer cells grown on Fn-EECMs that stain positive for EDA-Fn following fibril assembly promoted CSCs, though the role of the EDA domain has apparently conflicting reports in need of clarity. FIG. 3A demonstrates positive staining of EDA-Fn compared to an isotype control indicating bio-active type III-Fn domains, which was previously demonstrated as not conformationally available when adsorbed onto either 2D surfaces or polymeric fibers.

To assess assembly of Fn EECMs, nFn solutions were treated with 70 kDa proteolytic Fn fragments, which contain the 70 kDa N-terminus ($FnI_{1-9}$, $FnII_{1-2}$) implicated in the FnI-FnIII interactions required for assembly and historically used to block cell-mediated nFn assembly. The 70 kDa fragment was added in nFn solution used to produce EECMs at 0.176 mg/mL (approximately 5 molar excess) immediately prior to initiating hydrodynamic fibrillogenesis. FIG. 3B shows that fibril formation was perturbed, indicating that FnI-FnIII interactions are involved in EECM fibrillogenesis. Furthermore, disulfide reducing agents are commonly used to aid protein-based thiol chemistry; however, dimeric nFn is disulfide linked at the C-terminus and the dimeric form of the protein has been reported as a requisite for native assembly. Previously used for synthesis of HA-Fn hydrogels, 20 mM tris(2-carboxyethyl)phosphine (TCEP) at RT was added to nFn solutions for 15 min prior to the EECM coating process (2 h coating). Treatment with TCEP critically ablated the formation of fibrillar EECMs indicated by representative CLSM MIPs and area coverage image quantification, FIG. 3C. Furthermore, SDS-PAGE, FIG. 3D, confirmed that this treatment reduced nFn to its monomeric form but did not significantly fragment it further. Other commercially available nFn sources were assessed for both the presence of dimer as well as EDA-antibody binding, FIG. 4, further correlating the dimeric protein with fibril formation. Additionally, the SDS-PAGE of Fn-HA15 k conjugates (FIG. 3D) shows preservation of the dimeric protein after the bioconjugation method outlined in FIG. 1D (prior to fibril assembly).

To validate the proposed bioconjugation method and assess bound HA stability in cell culture conditions, nFn was treated with Gdn to unfold the protein and exposed to 2PT modified HA-2000 k (R-HA2000 kDa) and formed into EECMs via hydrodynamic fibrillogenesis, FIG. 3E. This was compared to unfolded Fn treated with unmodified HA and folded Fn with R-HA. Fn EECMs that were not exposed to any HA were used as a control. All EECMs were incubated at 37 C for 5 d in DPBS before a biotinylated HA-binding protein (HABP) probe was used to visualize and quantify the incorporation of HA via image analysis. All groups successfully formed fibrillar EECMs, but more HA in the unfolded/R-HA group was incorporated compared to either other group of nFn treated with HA.

FIG. 5 includes DIC counter images displaying similar amounts of fibrillar EECM in each group. Orthogonal quantification was performed using a platereader to assess fluorescence intensity of the HABP stain alone as well as the HABP/Fn ratios after co-staining with a non-specific polyclonal anti-Fn polyclonal antibody (pAb). Relative values are similar and statistical interpretation from all methods is identical, which suggests the methodology used here and throughout the chapter are robust. Furthermore, Fn EECMs treated with soluble, unmodified HA over the same 5 d time course, showed no difference compared to untreated Fn EECMs implying that fibrillar Fn does not sequester HA from solution in cell culture conditions. Additionally, the similarity of unfolded/native HA and folded Fn/R-HA, indicates that although HA is incorporated, it may be due to non-specific binding or steric intercalation of this very large molecule. Critically, other systems relying on intercalation of unmodified HA and ionic interactions for stabilization precludes stable incorporation of low Mw HA (6.4 kDa)

which may indicate those systems are acting as delivery platforms for soluble HA rather than presenting HA in a tissue-relevant, surface bound, insoluble form. Additionally, while there are some reports of Fn binding HA, this approach is not supported by our data. Finally, the HABP probe used suggests that minimally modified HA incorporated into Fn EECMs still possesses requisite structure to bind via Link-module (primary binding domain of such probes), discussed further in the following section.

Thiol Conjugation Strategy Enables Highly Controlled Presentation of Fibrillar Fn and HA in Three-Dimensions Incorporation of 2000 kDa and 15 kDa HA into EECMs with similar physical characteristics is advantageous for downstream cell studies. FIGS. 6A-6E summarizes physical characterization of the Fn-HA EECMs compared to Fn alone. For the remaining examples, all EECMs were produced across polymeric scaffolds with large rectangular pores coated with parallel fluid flow such that the resulting fibrils lack orientation using methodology previously reported. CLSM MIPs of large area scans of Fn-HA EECMs show that regardless of molecular weight, large multi-millimeter areas can be achieved with similar, non-oriented fibrillar morphology (FIG. 6A). Because of the importance of topology in cell-biology and tissue engineered systems, high-resolution confocal images were analyzed to determine fibril diameter. Fn, Fn-HA15 k, and Fn-HA2000 k EECMs all display remarkably similar, narrow distributions of fibril diameter, FIG. 6B. Furthermore, FIG. 6C displays 3D renders of approximately 70 μm×70 μm areas with approximately 20 μm of z-depth. FIG. 6D summarizes fibril diameter distributions and mass loading. All groups have approximately 1 μm diameters with 95% ranges from approximately 0.6 μm to 4 μm and skewed distributions tending toward slightly larger diameters. Diameter distribution summaries display exceedingly small changes between all groups.

Collectively, these data illustrate the physical nature of EECMs: coherent sheets comprised of fibrils with approximately 1 μm diameters are interconnected in a porous manner throughout the approximately 100 μm of polymer scaffold z-depth across approximately 5 mm×5 mm areas. Cells can then be seeded throughout EECMs simply by pipetting a solution over them. By comparison, other engineered technologies rely on modified/naturally derived hydrogels which physically encapsulate cells or only facilitate cells sitting atop the substrate. Physical constraint of cell in these systems may in and of itself play a role in the observations of growth modulation/phenotype. This shortcoming is overcome by employing porous EECMs.

Furthermore, relative amount between 15 kDa and 2000 kDa HA within EECMs is another parameter to control. To quantify mass loading, R-HA was simultaneously tagged with a Cy5 dye and Fn was labeled with a Dylight 488 dye. Fn EECMs and control samples were imaged using confocal microscopy. Control samples with known ratios of Fn-Dylight488 and HA-Cy5 were loaded into 4% m/m gelatin as a 3D matrix. To construct 3-point calibration curves, linear regressions were fit to intensity ratios of Fn-Dylight 488 and HA-Cy5 versus mass ratio, FIGS. 7A-7B. HA loading was calculated from Fn/HA EECM intensity ratios (imaged identically to the control cohort) using the linear fit equation. The mass loading data summarized in FIG. 6D highlights similar loading for both molecular weights; 61.1±2.9% (m/m) for HA-2000 kDa compared to 67.5±2.1% (m/m) for HA-15 kDa. Additionally, loading of both HA lengths in the fibrillar EECMs closely reflect the original reaction mixture (66% m/m HA in Fn) indicating the bioconjugation process is remarkably well controlled despite the approximately 130-fold difference in HA-length.

Finally, knowing that loading of both HA lengths was similar, Fn-HA EECMs were co-stained with HABP and an anti-Fn pAb to assess the binding affinity of HABP. The biotinylated-HABP used derived from bovine nasal cartilage, reports binding to HA>2 kDa and is composed of proteoglycans binding primarily through via the Link-module. HABPs that can be classified as Link-module binding include aggrecan, versican, hyaluronectin and CD44. Other important receptors including RHAMM bind through the B(X7)B motif, which would not be reflective of the data presented here. In FIG. 6E, platereader quantification of the HABP/aFn ratio shows that despite equal mass loading, HA-2000 k within EECMs has a higher binding affinity for a Link-module based probe. CLSM MIPs of these stained samples are shown in FIG. 7. Large, polymeric HA has been implicated in multi-valent interactions with HABPs potentially explaining CD44 clustering at cell membranes, and underpin why sandwich-like ELISA underestimate lower Mw HA bound on surfaces (<150 kDa) due to perturbing the flexibility necessary to adopt loop conformations for HABP binding. Hence, HABP affinity for the HA integrated into Fn EECMs reflects reported literature, where these differences may play a role in modulating cell behavior.

Fn-HA EECMs Display Tumor-Mimetic Morphology and Biochemistry

Laminin and collagen IV comprise the normal epithelium basement membrane, where escape from this and exposure to fibrotic ECM appears to confer phenotypic advantages that lead to dissemination of tumor cells. Seminal work by Mina Bissel's group shed light on the importance of the ECM in malignancies and Paolo Provenzano/Patricia Keeley paved the way for mechanistic and prognostic understanding of collagen reorganization in breast tumor stroma. It is clear that intratumoral cellular and ECM heterogeneity is correlated with poor prognosis and is implicated in facilitating metastatic dissemination of tumor cells. Disseminating tumor cells commonly home to the bone marrow as a site for metastasis and recurrence, where cells secrete high levels of HA as a normal component of the bone marrow tissue niche. Stromal cells are implicated as the architects of tumor ECM, and bone-marrow derived mesenchymal stem cells (BM-MSCs) are known to be recruited to the primary tumor and contribute to metastatic spread.

To compare the inventive engineered system to a heterogenous environment reflective of intratumoral heterogeneity, a co-culture model comprised of tumor-cells (T47Ds or MCF7s) and bone-marrow cells (HS27a or HS5) was utilized to investigate the role of ECM heterogeneity. HS27a and HS5 bone marrow stromal cells are used as analogues for BM-MSCs in cancer research, where HS5s have been verified as representative analogues for primary MSCs. Furthermore, this co-culture system has revealed that a greater fraction of tumor cells co-cultured with BM-MSCs resided in a quiescent state with increased metastatic potential. Bulk RNA-sequencing revealed that both HS27a and HS5s in co-culture generally expressed higher levels of HAS2 than MCF7s/T47Ds in the correlated co-culture, FIG. 8A. Interestingly, HS5s had less significant changes in expression of FN1 in co-culture compared to MCF7s in the respective co-culture. Additionally, MCF7s in co-culture with HS5 and HS27a had a marked increase in the expression of both HAS2 and FN1 compared to MCF7s in monoculture. To investigate these transcriptional signatures at the protein level, co-cultures of MCF7s/HS5s were fixed and decellularized to assess their stability and compared to EECMs, FIG. 8B. Co-cultures showed substantial deposition of fibrillar, EDA+ Fn as well as HA, with clear co-localization of fibrillar EDA-Fn with HA. Additionally, much of the HA remained intact following decellularization indicating that it was insoluble/tissue bound. Finally, Fn-HA EECMs display similar fibrillar morphology to cell secretions where much of the HA and Fn signal co-localizes (displayed in merge channel) with distinct regions and nodes similar to the co-cultures.

HAS2 expression in breast tumor cells has been correlated with invasive phenotypes and reported as encoding for high Mw HA (>1,000 kDa). Furthermore, in breast cancer upregulation of FN1 expression is reported alongside EMT/CSC-enrichment in HA-related investigations, but FN1 is used as a marker for EMT and has not been investigated extracellularly. In lung and other tissues, deposition of Fn and HA have been correlated with fibrotic remodeling but the significance underpinning their co-secretion is elusive. In the context of breast cancer the dual presentation of HA and Fn as fibrotic extracellular components capable of influencing cell fate warrants further investigation.

Fn-HA EECMs Allude to Complex Role of Protein-Glycan Regulation in Tumor Tissue.

Figures 9A, 9B, 9C, 9D, 9E, 9F, 9G, 9H, 9I, 9J:
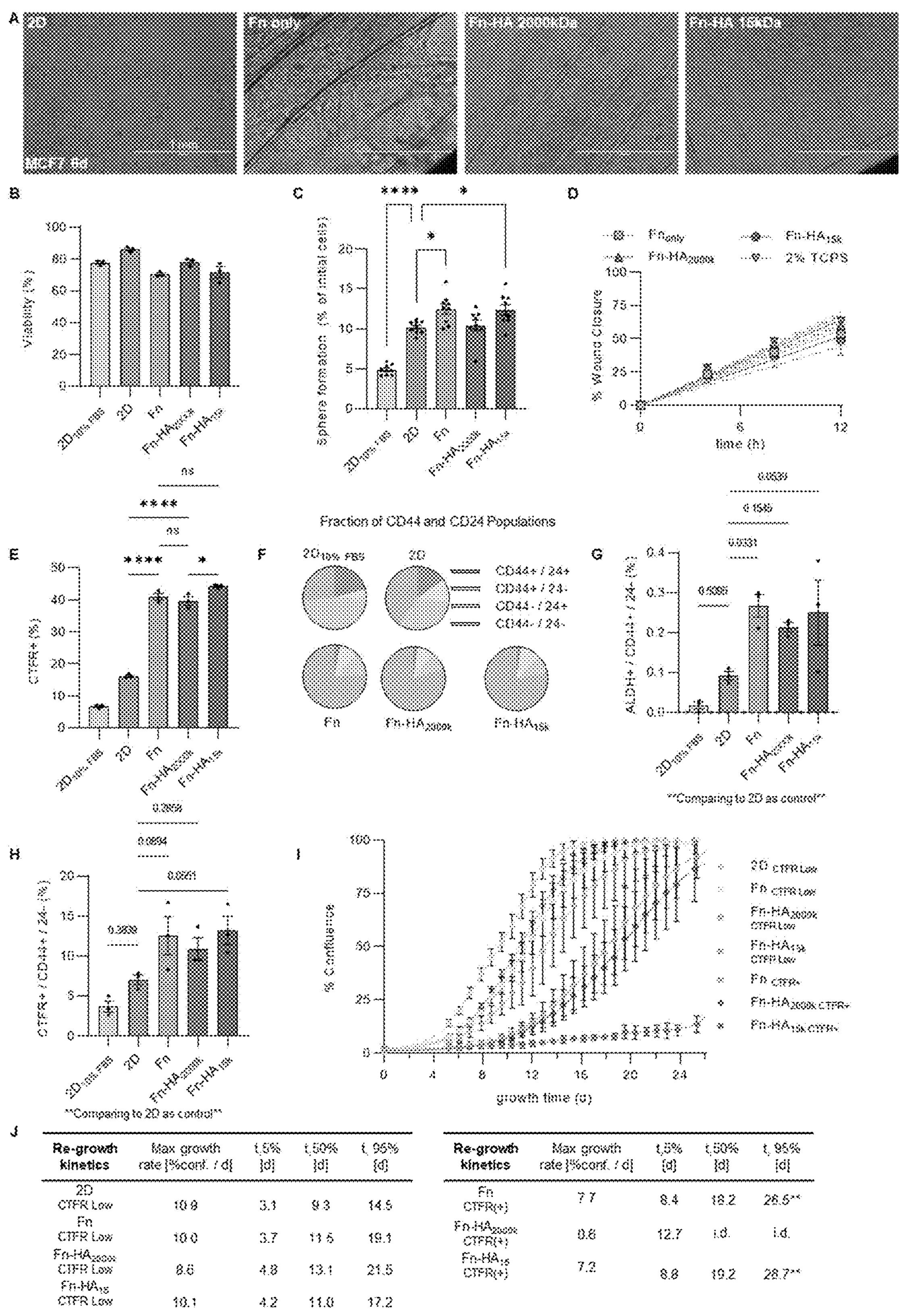
Figures 10A, 10B, 10C, 10D:
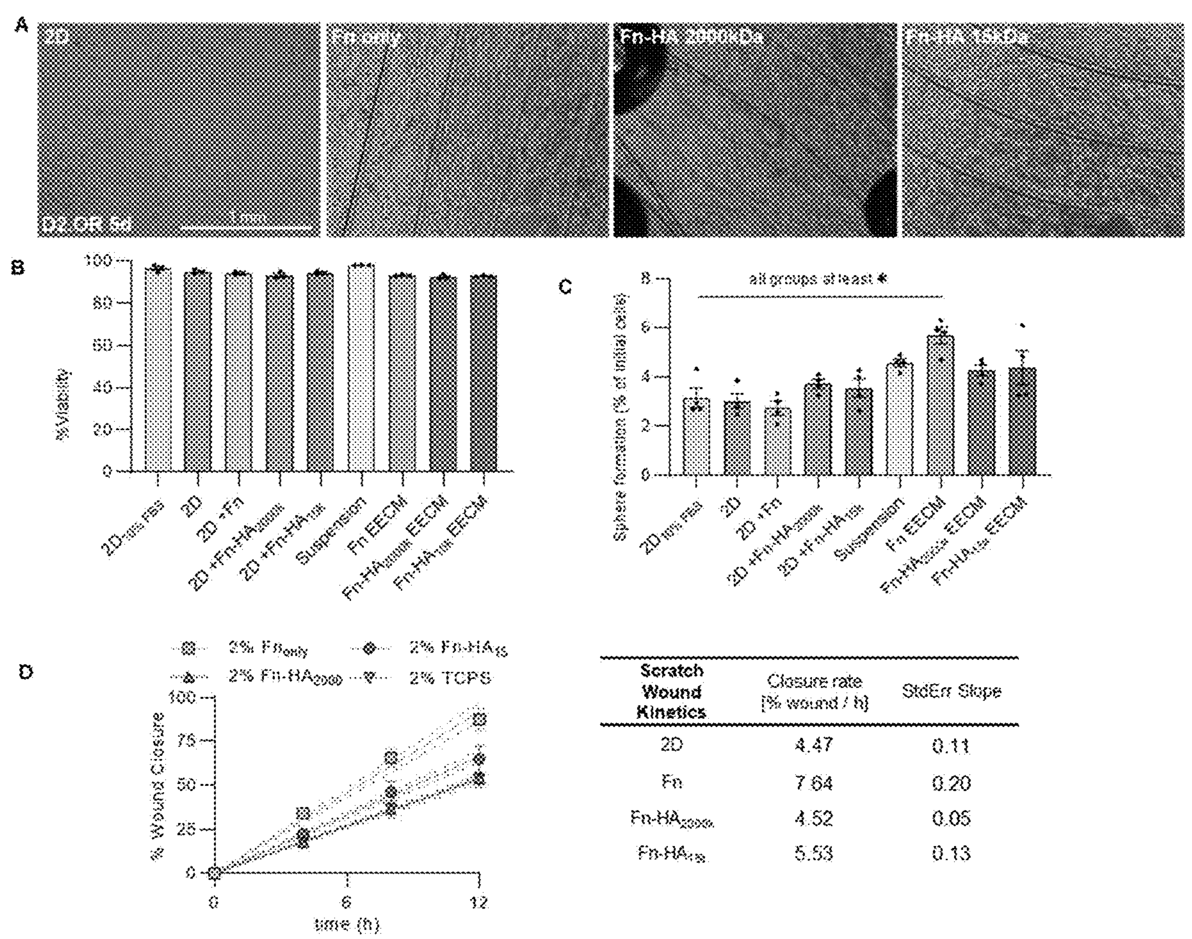

With Fn-HA EECMs established as well controlled, tumor-mimetic microenvironments, the hypothesis that HA present in the tumor stroma would epigenetically regulate cell phenotype and influence metastatic potential of tumor cells is investigated. Toward this, MCF7s were grown in low FBS (2% v/v) on EECMs (Fn, Fn-HA2000k, Fn-HA15k) and compared to TCPS (2D) in 2% v/v FBS as well as standard (10% v/v FBS). FIG. 9A shows in bright field after 6 d that cells were approaching confluence without any obvious changes in growth dynamics or morphology indicative of unhealthy cells. This was supported by viability measurements where all groups were similar and above 70%, FIG. 9B. Interestingly, MCF7s primed on different environments displayed differential sphere formation capacity which would generally indicate upregulation of tumor-initiating stem phenotypes, shown in FIG. 9C. Here Fn EECMs significantly upregulated sphere formation, assessed at 15 d, compared to 2D. Fn-HA2000k EECMs where not different than 2D, yet MCF7s primed on Fn-HA15k EECMs were significantly above 2D and similar to Fn EECMs. MCF7s cultured on different conditions were then replated into 96 well plates and allowed to proliferate for 4.5 d before assessing scratch wound kinetics to assess invasive/migratory phenotypic changes, which revealed no striking differences in the epithelial MCF7 cell line FIG. 9D.

To investigate the role of various growth environments on proliferation and stemness, a dye retention assay with Cell Trace Far Red (CTFR) was performed using flow cytometry. This assay stratifies proliferating and non-proliferating cells because lower dye signal arises from a greater number of cell divisions. Dye retention assays have also been used to identify breast CSCs and normal mammary stem cells. This revealed that despite robust growth on EECMs observed under brightfield microscopy during the 6 d of growth (FIG. 9A), there were substantial populations of high dye retaining (CTFR+) cells on the 3D environments compared to 2D FIG. 9E. Here FN-HA15k EECMs had a nominal, but statistically significant increase over Fn-HA2000k EECMs.

Next, CD44+/CD24− and ALDH+ which are used to denote breast CSCs subpopulations that are more mesenchymal and epithelial is investigated, respectively. These markers were assayed alongside CTFR via flow cytometry. Surprisingly, CD44+ populations did not change across 3D groups, but CD24 was significantly decreased following culture on all EECMs compared to both 2D controls, FIG. 9F. Neither mesenchymal-CSC (CD44+/24−) nor epithelial-CSC (ALDH+) populations differed across MCF7s grown on 2D or 3D EECMs in low serum. Interestingly, dual-positive CD44+/24−/ALDH+ populations were higher on Fn and Fn-HA15 k (p=0.0331, p=0.0539, respectively) than was Fn-HA2000 k (p=0.1545) when compared to 2D (FIG. 9G). Because of the dramatic increase in dye retention, the intersection of CTFR+/CD44+/24− populations was assessed which displayed similar trends. When compared to 2D, Fn (p=0.0894) and Fn-HA15 k (p=0.0551) were approaching significance, but Fn-HA2000 k (0.2858) was not significant.

Next to evaluate whether growth characteristics were altered by the initial growth substrate, CTFR+ cells were sorted from CTFR low cells and re-plated on standard TCPS 96 well plates and grown in full serum (10% v/v) media, FIG. 91. Growth kinetics were determined by non-linear fits and summarized in FIG. 9J. These data showed that of $CTFR_{low}$ groups, 2D regrowth was fastest (10.9% conf/d, $t_{50\%}$=9.3 d), followed by Fn-HA15 k and Fn EECMs (10.1% conf/d, $t_{50\%}$=11.0 d|10.0% conf/d, $t_{50\%}$=11.5 d, respectively) and then Fn-HA2000 k (8.6% conf/d, $t_{50\%}$=13.1 d). Not surprisingly, CTFR+ cells grew slower than the $CTFR_{low}$ counterparts, but intriguingly CTFR+ MCF7s primed on Fn-HA2000 k samples displayed little growth over the time course assessed.

Given the interesting changes in dye-retention, regrowth and phenotype with MCF7s, D2.OR cells were grown on the different environments as this cell line has been characterized as modeling metastatic recurrence in vivo but not in vitro unless grown on a 2.5D environment (atop Matrigel). Similar to MCF7s, D2.ORs displayed attachment and slow proliferation in low serum conditions, FIG. 10. All groups had high viability after culture for 5 d on all substrates (>90%), FIG. 10B. Additional 2D control groups included TCPS (2D) coated with Fn, Fn-HA2000 k, and Fn-HA15 k to explore the role of conformation of the protein-glycan conjugates. Cells grown in mammosphere media (suspension) were used as a 3D control because mammosphere culture is reported to enrich for stem-cells as well as non-proliferating cores. Interestingly, only Fn EECMs showed significant increases in sphere formation compared to all 2D groups but not any 3D groups FIG. 10C. Suspension culture was statistically significantly higher than 2D+Fn but not any other groups. Notably, Fn and Fn-HA conjugates coated on 2D surfaces did not impact sphere formation. Furthermore, scratch wound assay showed differences in wound closure kinetics following 3d of regrowth on TCPS before beginning the assay, FIG. 10D. D2.ORs primed on Fn displayed the fastest wound closure (7.64% wound/h), followed by Fn-HA15 k (5.53% wound/h) and finally Fn-2000 k and 2D (4.52% wound/h|4.47% wound/h, respectively).

Figures 11A, 11B, 11C, 11D, 11E, 11F:
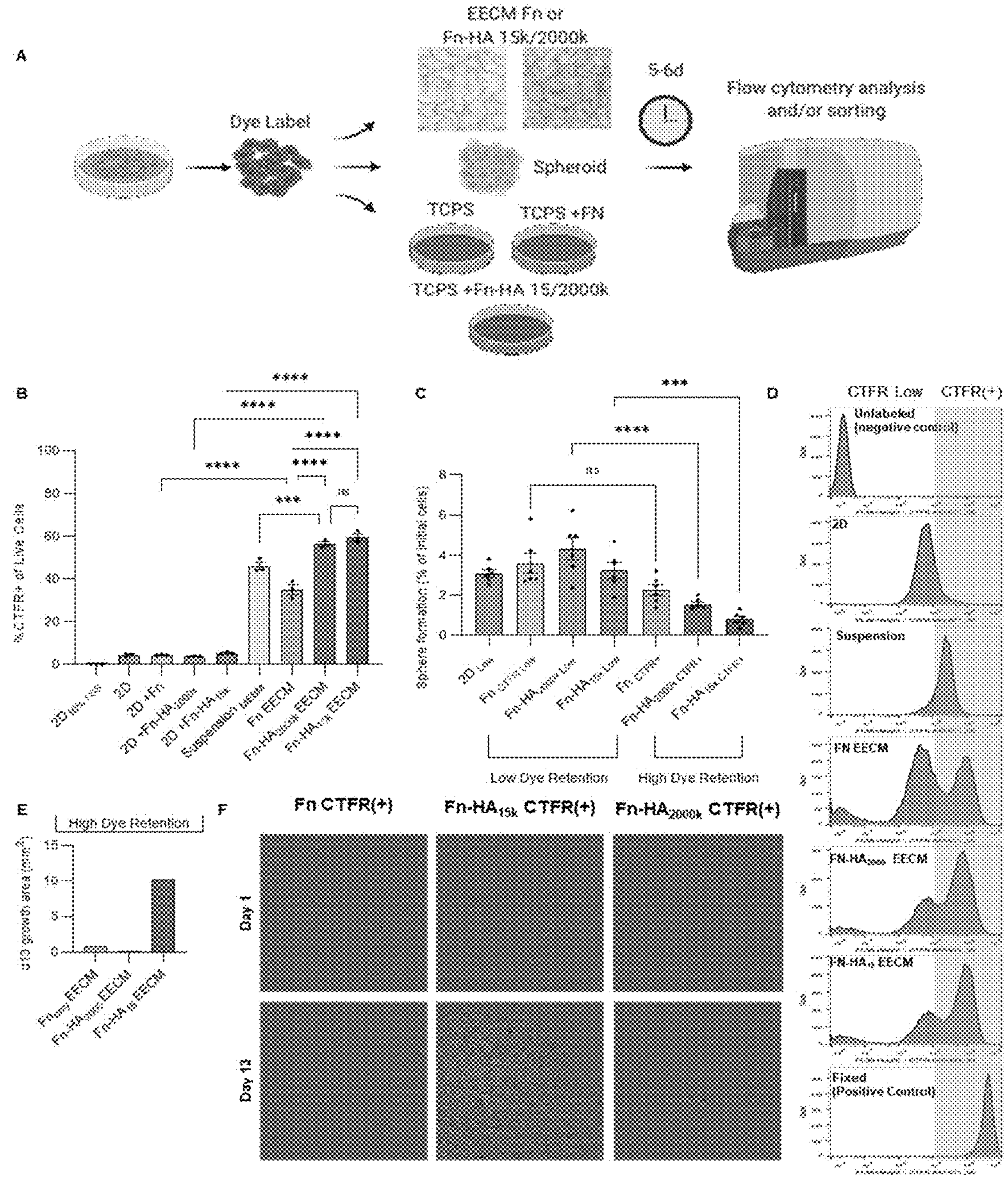
Figures 12A, 12B, 12C, 12D, 12E, 12F:
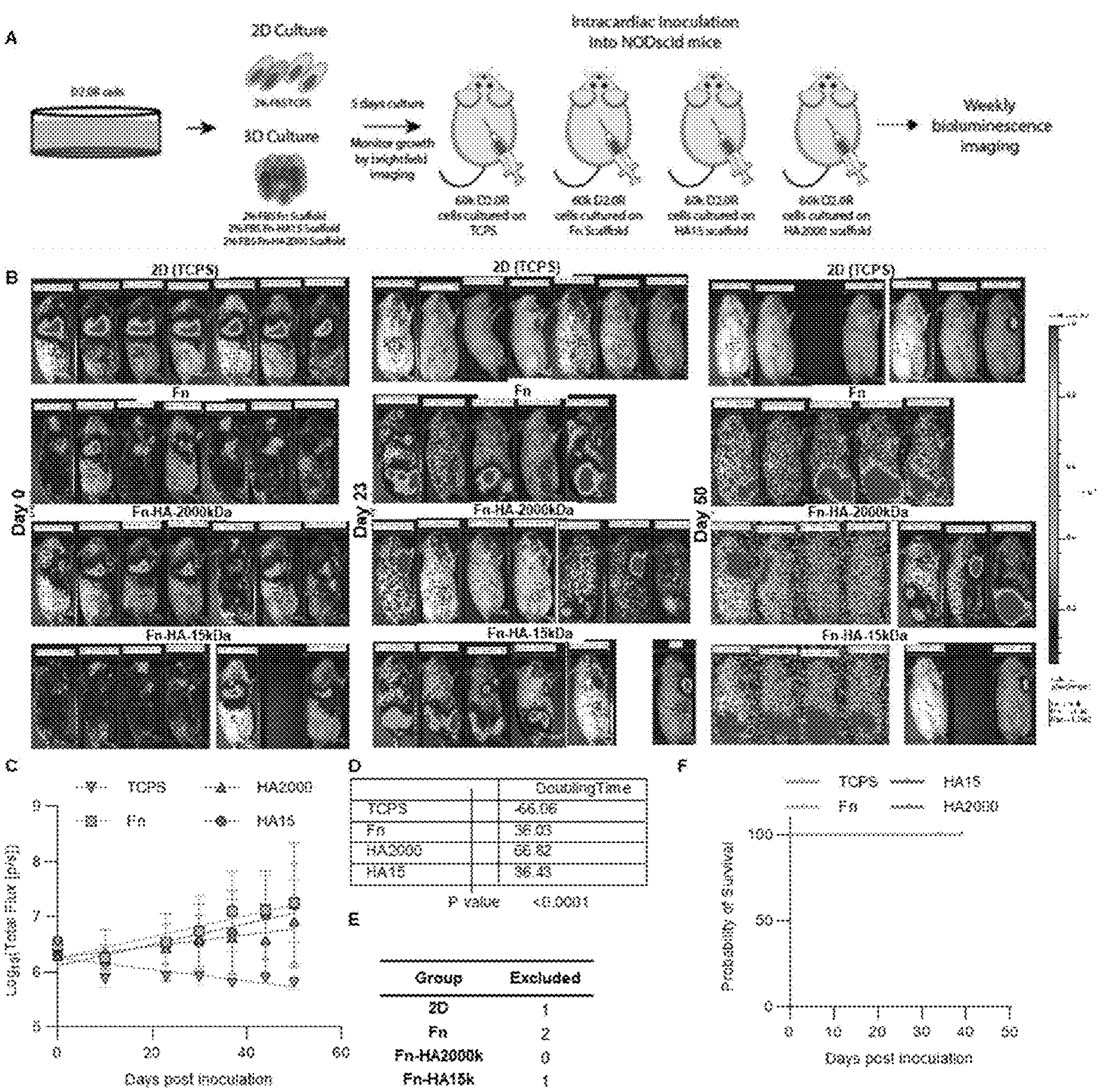

To characterize growth characteristics, the dye retention assay was again utilized, displayed graphically in FIG. 11A. With D2.ORs, 3D EECM conditions again supported substantial increases in CTFR+ populations compared to all 2D groups (FIG. 11B). Furthermore, both Fn-HA EECMs displayed significantly higher dye-retention than either suspension culture or Fn EECMs. Fn-HA15 k again showed a nominal, but not statistically significant increase in CTFR+ populations compared to Fn-HA2000 k. Fn and Fn-HA conjugates coated on 2D surfaces did not impact dye retention compared to other 2D samples. High dye retaining cells were sorted from the lower dye retention (CTFR+vs CTFR low) and assessed via sphere formation assay, FIG. 11C with sorting gates represented in FIG. 11D. Unexpectedly, high dye retaining cells, especially those primed on Fn-HA EECMs, had a marked decrease in sphere formation efficiency compared to their low dye retaining correlates.

Histograms of the CTFR signal shows that when cultured on 2D or in suspension culture, D2.ORs have a singular distribution of dividing cells (FIG. 11D). These distributions shift down from the positive control differentially, indicating a change in proliferative rate, which was unsurprisingly faster for 2D than suspension. Remarkably, when grown on EECMs, three distinct proliferative populations are observed. The highest dye retaining peak likely indicates a quiescent population that had divided at least once, as the peak maxima are lower than the positive control but interestingly slightly higher than suspension culture. There is then a moderately proliferating bulk that aligns with 2D, as well as a highly proliferative population that has lost all dye (aligned with unlabeled control). The quiescent CTFR+ group is upregulated in both Fn-HA EECMs compared to Fn EECMs. Critically, these tri-modal growth populations were not observed for any of the 2D groups coated with Fn or Fn-HA conjugates. This indicates that conformationally active, fibrillar fibronectin promotes markedly heterogeneous growth where the presence of HA facilitates more quiescent cells. During the sphere formation assay, cells in the CTFR+ groups sorted from EECMs (FIG. 11C) appeared to reside in a single-cell, quiescent state instead of forming spheres. These cells were filtered from spheroids using a 35 μm flow tube and replated onto TCPS 96 well plates and cultured in standard media (DMEM, 10% FBS). Strikingly, D2.ORs primed on Fn-HA15 k EECMs for 6 d that resided in a single-cell state during 18 d in non-adherent, serum free mammosphere culture were able to re-activate on TCPS in 10% FBS and displayed substantial growth not seen by those cells primed on either Fn or Fn-HA2000 k EECMs.

Notably, the lack of differences in growth populations in 2D+Fn-HA (15 k/2000 k) indicates that HA alone in these models is not sufficient to direct growth kinetics, and is instead catalyzed by the presence of conformationally active fibrillar Fn. The significance of fibrillar Fn and not 3D culture alone is supported, as D2.ORs grown in suspension did not give rise to multi-modal growth populations. Finally, the lack of differences in sphere formation of D2.ORs cultured on Fn/Fn-HA coated 2D substrates (FIG. 10C) all collectively support the notion that conformational activity of fibrillar Fn is key to both the stem phenotype and differential growth kinetics observed across two cell lines and various assays. We previously showed that Fn coated on 2D surfaces did not display active binding for cellular Fn mAbs, which indicates conformationally sensitive type-III domains are exposed in the fibrillar form and may, in part, explain this finding. Interestingly, Barney et al. reported cells capable of entering long term in vitro dormancy were those that organized fibrillar-Fn rich ECMs and had heterogeneous populations of proliferating/non-proliferating cells. This finding is consistent with the observations reported here that fibrillar Fn itself is believed to play a key role in producing quiescent/highly proliferative cells. Toward the differences in sphere formation for CTFR+ cells, Cicalese et al. proposed a model in which CSCs may divide symmetrically to produce two additional stem cells with increasing asymmetric divisions to produce progenitors overtime which would lead to CSCs with different levels of dye retention. Even though high dye retaining D2.ORs had lower sphere formation, it is possible that while not sphere forming, the high dye retaining D2.ORs from Fn-HA15 k environments adopted a phenotype whereby long-term survival advantages are conferred but not captured in vitro by the mammosphere assay.

Therefore, to vet significance of these in vitro findings and directly probe the metastatic colonization of cells primed on different environments, intracardiac injections were performed using NODscid mice and D2.ORs engineered with a click beetle green (CBG) luminescence reporter. Dissemination and growth kinetics are being assessed using Bioluminescence imaging (BLI), shown schematically in FIG. 12A, and overall survival will be reported. BLI up to day 50 shows similar trends to in vitro studies for the 3D groups in that Fn and Fn-15 k EECMs have similar, faster overall doubling times (36.03 d and 36.43 d, respectively) compared to Fn-2000 k (66.82 d). At this point in time, cells primed on 2D regressed indicated by a negative doubling time. Notably, interesting phenomena have been observed qualitatively by inspection such as D2.ORs primed on Fn EECMs that colonized the lower body (likely bone metastases) in at least one case are regressing over the first 50 d (mouse #1 in Fn group), which does not appear to be the case in Fn-HA 15 k or Fn-HA 2000 k. Though it is too early to draw conclusions, as this assay is expected to take up to 100+d, because D2.ORs are less aggressive in vivo than other cell lines more commonly studied in vivo (i.e. MDA-MB-231) and make them an ideal candidate for resolving differences in phenotype conferred by in vitro culture on EECMs.

Collectively, Fn influenced cells to display hallmarks of stemness upregulation in vitro as noted by functional sphere formation assays and phenotyping. Furthermore, Fn consistently caused upregulation of dye retaining populations, which has been indicative of CSC enrichment. While the presence of high Mw (2000 kDa) HA seemed to perturb these functional phenotypes, it did not completely reverse them. Additionally, fibrillar Fn clearly impact growth dynamics as assessed by dye retention, regrowth assays and metastatic growth in vivo wherein high Mw HA (2000 kDa) leads to overall slower proliferating cells or cells that cannot reactivate in standard culture conditions, while low Mw 15 kDa HA facilitates recovery of growth. Collectively, these data imply that fibrillar Fn induces bipotent CSCs implicated in metastasis as well as heterogeneous growth populations, while co-presentation of low Mw HA may confer additional phenotypic advantages of long-term survival implicated in metastasis/recurrence.

The present disclosure thus contemplates stable, fibrillar Fn/HA mimics that are representative of tumor-associated ECM produced via a controlled disulfide conjugation strategy at FnIII with minimally modified HA. Fn fibril assembly can be induced with hydrodynamic fibrillogenesis and is apparently not reliant on domain interactions or disulfide bonds involving FnIII. Rigorous characterization was employed to ensure the Mw of the commercially available HA was as reported and remained unmodified following chemical derivatization. A minimal substitution rate was chosen to statistically preserve many subunit blocks necessary for HA-binding. It is demonstrated that Fn EECM assembly followed established characteristics from cell secretion models in that the dimeric protein was important and assembly was perturbed by treatment with the 70 kDa N-terminal fragment. The bioconjugation methodology developed to produce Fn-HA EECM conjugates is remarkably well controlled for both high molecular weight (2000 kDa) and low molecular weight (15 kDa) HA, despite very large differences in molecule size. This was demonstrated by confirming HA presentation in fibrillar ECM substrates reflected the original reaction mixture even after purification and fibril assembly. The physical characteristics of Fn EECMs or Fn-HA EECMs are well controlled where they are all porous, 3D, have narrow (approximately 1 μm-4 μm) fibril diameter distributions and are able to cover large areas and facilitate unconstrained cell growth throughout the constructs. Furthermore, Fn-HA EECMs display binding by a Link-module probe in a Mw dependent manner reflective of literature reports where high Mw HA had substantially increased binding compared to low Mw HA.

To validate the clinical motivation, a co-culture model reflecting BM-MSC recruitment to the primary tumor demonstrated increased deposition of tissue bound HA and Fn at the transcriptional and protein level. Fn-HA EECMs were then demonstrated as biochemically and morphologically similar to the secreted ECM of tumor cell/MSC co-cultures but are produced with definable, purified components compared to the diverse mixtures that constitute cell-secreted ECMs.

Tumor-mimetic EECMs were then employed to assess epigenetic regulation of tumor cells grown in Fn, High Mw HA-rich and low Mw HA-rich environments. Significant increases in sphere formation efficiency of MC7s primed on Fn and Fn-HA15 k EECMs were found indicating upregulation of CSCs. Additionally, the trends in sphere formation, did not correlate with CD24 status, CD44+/24−, or ALDH+ populations but instead correlated with dye retention (CTFR+), CTFR+/CD44+/24−, and ALDH+/CD44+/24− populations. Bipotent breast CSCs are thought to have greater metastatic potential and may be a more reliable marker to transcend subtype/cell line differences. Recent compelling single cell lineage tracing in pancreatic cancer has revealed EMT extremes are less metastatic than EMT hybrids, which is consistent with the proposed model for breast CSCs existing on this epithelial to mesenchymal spectrum. Additionally, MCF7 growth dynamics were modified following only 6 days of growth where Fn-HA15 k and Fn EECMs showed faster regrowth than Fn-HA2000 k, and CTFR+ MC7s grown on Fn-HA2000 k did not grow after nearly 4 weeks of culture.

Fibrillar fibronectin also induced higher sphere formation in D2.ORs, which was not seen when the protein and protein-glycan conjugates were coated onto TCPS. For this more mesenchymal cell line, fibrillar Fn also induced a stark increase in scratch wound closure after cell populations proliferated for 3 days indicating inherited phenotypic changes. High Mw HA appeared to repress this phenotype while low Mw HA allowed for partial recovery of this invasive/migratory phenotype. Most interestingly, conformationally active, fibrillar fibronectin induced disparate growth populations comprised of some entering quiescence, moderately proliferating cells, and rapidly proliferating cells. This was not observed when this cell line was grown on 2D or even when grown in 3D spheroids. The presence of high and low Mw HA facilitated more cells entering a quiescent state, where those cells grown in the presence of low Mw HA may have a greater capacity for survival/reactivation. Thus far, up to day 50 whole-body in vivo growth kinetics of D2.ORs reflect the influence on growth observed in vitro with MCF7s whereby cells primed on Fn and Fn-HA15 k are growing more rapidly than HA-2000 k.

Taken together, the cell studies support the notion that fibrillar Fn induces bipotent CSC phenotypes, as well as growth phenotypes that are implicated in metastasis/recurrence. These changes conferred inherited functional differences in cells reflected by downstream assays performed days (scratch), weeks (sphere formation/regrowth) or months (intracardiac injections) following priming of tumor cells for only 5-6 days on different environments. Furthermore, unique growth characteristics on fibrillar Fn reasonably correlate with a recent report that fibrillar Fn is involved in the entrance of dormancy, but our studies were not taken out to the long culture times employed by Barney et al, but instead indicate potential entrance into quiescence. Also important to interpretation, even at an approximate 2:1 mass ratio (HA:Fn) high Mw HA generally suppressed bipotent phenotypes induced by Fn in vitro, but it was not sufficient to completely reverse these phenotypes in all cases which challenges the general summary of high Mw HA in tumor microenvironments reflecting "healthy" tissue.

Interestingly, these data imply conflicting roles of high Mw HA/fibrillar Fn and potentially cooperative roles once the glycan has been degraded away to where only low Mw fragmented HA remains, where fibrillar Fn appears to be the catalyst of modulating tumor cell phenotype.

The role of HA in tissue biology is one of incredibly disparate reports ranging anywhere from 117 kDa to 6,000 kDa being described as "high" where others define 100-1000 kDa as lower/intermediate. This is of course is context dependent, but there exist discrepancies of reports within the same tissue systems, which is especially misleading for those beginning research in pathogenic tissue contexts. From HA's discovery in vitreous fluid in 1934, to the few studies in the 1970s implicating it in embryonic development, it was not until the 1990s and early 2000s that heavy investigation began into its role the tumor microenvironment. Hence, the comparative baseline for modeling these pathogenic tissue systems is being amassed and can be aided by engineered technologies. While our understanding of soluble HA, particularly oligomeric fragments, in tumor progression has grown more advanced, there is likely still much to learn of the role of HA in proteinaceous fibrotic tissues. Expanded understanding of in vitro and in vivo tumor cell regulation utilizing precisely defined engineered models offer a valuable path forward toward clarifying seemingly disparate reports.

Ultimately, proteins and glycans are complex molecules whose tertiary/quaternary structure define their presentation and thereby their function. Cells do not simply bind fragmented peptide domains or glycan fragments when engaging intact tissues. Therefore, this should not be overlooked when engineering biomaterials, as it may have unintended consequences in modeling native tissue biology; hence, defining the level of complexity needed is at the crux of employing reductionistic models. While HA hydrogels have a well-established and undeniable benefit in regenerative engineering, their use as models for pathogenesis is currently limited due to a lack of tumor tissue-relevant mimicry.

The inventive engineered fibrillar Fn constructs decorated with HA of defined length provided by certain aspects of the present disclosure fill this unmet need and can be used to further elucidate HA's complex role in the tumor microenvironment. Fn and HA may have simultaneous cooperative and conflicting roles in an Mw dependent manner that are important in regulating tumor cell fate to confer survival and facilitate metastasis. With further investigation of the Fn and HA constructs reported here, there is opportunity to expand fundamental knowledge of tumor progression and rapidly manufacture reproducible, defined 3D models. These HA constructs may be used clinically to repress invasive phenotypes by implantation, to improve drug screening by enriching metastatic phenotypes, or to improve patient cell expansion ex vivo.

EXAMPLES

Protein Coating

Polymer scaffolds were coated with human fibronectin (Corning Inc, Corning, NY, Sig) that was diluted to a concentration of 111 μg mL-1 in calcium/magnesium free Dulbecco's phosphate buffered saline (DPBS) for 2 h, as described previously. Briefly, TPSs were suspended with the center of the scaffold at the solution/air interface, and with the steel-frame/scaffold construct centered on the long-axis of a low-binding microcentrifuge tube (Biotix, San Diego, CA, USA). The TPSs were then gently sheared in an Eberbach EL655.I Incubator tumbler (Eberbach Corp., Belleville, MI, USA) at 8 rotations per minute (RPM) and 30° C.

For assembly blocking experiments, 70 kDa Fn fragment was added to native dimeric Fn (0.176 mg/mL 70 kDa fragment/0.106 mg/mL in 0.9 mL with DPBS as a solvent) before assessing the formation of fibrillar EECMs via hydrodynamic fibrillogenesis. Brightfield images were gathered to assess fibril network formation.

Cell Culture

MCF7s and D2.ORs were cultured in high-glucose Dulbecco's Modified Eagle Medium (DMEM) supplemented with 10% (v/v) fetal bovine serum (FBS) and 1% (v/v) antibiotic-antimycotic (ThermoFisher Scientific, Waltham, MA, USA). Cells were tested and confirmed negative for mycoplasma before studies were performed using a Lonza MycoAlert™ kit (Lonza, Basel, Switzerland) in accordance with the manufacturer recommendations.

Fluorescence Staining

In order to visualize the fibronectin for directionality analysis, unmodified Fn was blended with Dylight-650 conjugated Fn (5.6% v/v). The dye used was an NHS-ester DyLight-650 and was prepared in accordance with manufacturer recommendations (ThermoFisher Scientific, Waltham, MA, USA). In the cell spreading assay, nuclei were stained with Hoechst 33342 (ThermoFisher Scientific, Waltham, MA, USA), and actin with Alexa Fluor™ 488 phalloidin (ThermoFisher Scientific, Waltham, MA, USA). The Fn matrices were stained with anti-fibronectin polyclonal antibody F3648 (Sigma-Aldrich, St. Louis, MO, USA).

Decellularization

If cells were removed from Fn networks to visualize the remaining protein matrix, samples were decellularized in a protocol adapted from Lu et al., Comparison of decellularization techniques for preparation of extracellular matrix scaffolds derived from three-dimensional cell culture. J. Biomed. Mater. Res. Part A 100A, n/a-n/a (2012), the relevant portions of which are incorporated herein by reference. Samples were washed with phosphate buffered saline (PBS), then deionized (DI) water, and immersed in a solution of 0.1% Triton X 100 with 1.5 m KCl in $50\times10^{-3}$ m Tris buffer on a slow-moving shaker for two hours at 4° C. Samples were washed in $10\times10^{-3}$ m Tris buffer, followed by DI water for one hour each. The remaining protein matrix was fixed and stained via ICC protocol.

HA Synthesis Materials

HA, with the molecular weights of 8-15 kDa and 1750-2000 kDa were purchased from Contipro. Dowex® 50W-X8, 4-Methylmorpholin (NMM) and 2-chloro-4,6-dimethoxy-1,3,5-triazine (CDMT) were purchased from VWR. (S)-2-Pyridylthio cysteamine hydrochloride from abcr and the Cy-5 Amine (CAS 1807529-70-9) from abcam.

HA Synthesis and Purification

The reaction procedure was adapted from Bergmann et al., Hyaluronic Acid Derivatives Prepared in Aqueous Media by Triazine-Activated Amidation. Biomacromolecules 8, 2190-2195 (2007), the relevant portions of which are incorporated herein. The carboxylic acid moiety was derivatized as it follows: Hyaluronic acid sodium salt was dissolved in MilliQ water (5 mg/mL, pH 6.85) and mixed with Dowex H+. The mixture was stirred firmly at room temperature for 1 h, then filtered by tangential flow filtration, the solution (pH 2.85) was freeze-dried to obtain hyaluronic acid protonated form. Hyaluronic acid (0.158 g, 0.415 mmol, 1.00 equiv.) was dissolved in 150 mL of MilliQ water in a round-bottomed flask followed by the dropwise addition of 50 mL of acetonitrile while stirring. To the solution was added 0.01470 g (0.0159 mL, 0.145 mmol, 0.350 equiv) 4-methylmorpholine (NMM). The solution was then cooled down to 4° C., and 0.0137 g (0.0785 mmol, 0.189 equiv) of 2-chloro-4,6-dimethoxy-1,3,5-triazine, was added and stirred at room temperature for 1 h. Subsequently, the solution was mixed with the respective amines. In order to obtain HA-2PT-Cy5, 0.0137 g (0.0619 mmol, 0.149 equiv) of (S)-2-Pyridylthio cysteamine hydrochloride (2PT) and were added and 0.0109 g (0.0166 mmol, 0.0400 equiv.) Cy-5 amine were stirred for 20 h at room temperature. To only obtain non-labeled HA-2PT, the same reaction procedure was executed despite leaving out the Cy-5 amine. Finally, Dowex saturated sodium form was added to the reaction mixture, stirred for 30 mins and then filtered through tangential flow filtration (TFF) purification from Repligen, with 3 kDa cutoff hollow fiber mPES MidiKros® filter modules for the purification of 8-15 kDa modified HA and 300 kDa cutoffs for the 1750-2000 kDa HA. After was freeze-drying and lyophilization HA-2PT and HA-2PT-Cy5 were obtained (yields).

HA-Fn Bioconjugation

Dimeric, plasma derived Fn (Corning or Sigma) was dialyzed into 0.05M borate (pH 8.5) at a starting concentration of 2.5 mg/mL, typically resulting in approximately 2 mg/mL Fn in borate. 2PT-modified-HA was dissolved at 10 mg/mL in 0.05M borate buffer. Borate buffer and 8 M Gdn was added such that the resultant mixture was 4 M Gdn, approximately 1.4 mg/mL 2PT-HA and approximately 0.7 mg/mL Fn. In series, the dialyzed Fn was diluted with borate buffer, then Gdn was added for approximately 5-10 min, followed by 2PT-HA to complete the reaction mixture. Argon was sprayed in the cap of the microcentrifuge tube (the reaction vessel) through a sterile filter, and the reactions were gently shaken at 30 C for approximately 18 h. Reaction mixtures were then isolated with a syringe a dialyzed with Slide-a-lyzer (Thermoscientific) cassettes with cutoffs lower than each molecular weight (10 k for 2000 kDa, and 3 k for 15 kDa). Fn content was analyzed in the resultant mixture using A280 measurements and an in-lab calibration curve accumulated over time across multiple lots of product.

Statistics

Three or more replicates were used to generate the data throughout the paper unless otherwise noted. For statistical analyses either custom Graphpad Prism (v 8.4.3, San Diego, CA, USA) were used. The Shapiro-Wilks Test was used to determine whether the data follow a normal distribution. Equal variance was assessed using Levene's test. When comparing three or more groups, if the data are not normal or do not have equal variance between groups, then the Kruskal-Wallis H-test (n>5) followed by post-hoc analysis with the Dunn's multiple comparisons test was performed to assess levels of statistical significance among the groups. For comparing two groups, the Mann-Whitney U Test was performed if the data were non-parametric and a T-test if data were parametric or the Holm-Sidak Multiple t-test. Throughout the manuscript: p≤0.05*, p≤0.01**, p≤0.001

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A cellular support system comprising:

a three-dimensional scaffold structure comprising at least one void; and a suspended fibril spanning across the at least one void in the three-dimensional scaffold structure, wherein the suspended fibril comprises at least one extracellular matrix protein comprising at least one disulfide or thiol group and at least one functionalized glycan bonded to the extracellular matrix protein via the at least one disulfide or thiol group and the suspended fibril is capable of supporting cells and promoting three-dimensional cellular growth.

2. The cellular support system of claim 1, wherein the void has a major dimension of greater than or equal to about 0.1 micrometers to less than or equal to about 5 centimeters.

3. The cellular support system of claim 1, wherein the at least one extracellular matrix protein comprises fibronectin.

4. The cellular support system of claim 3, wherein the suspended fibril further comprises one or more proteins selected from the group consisting of: collagens, laminins, tenascins, elastin, vitronectin, periostin, and combinations thereof.

5. The cellular support system of claim 1, where the at least one glycan comprises a glycosaminoglycan.

6. The cellular support system of claim 5, wherein the glycosaminoglycan comprises hyaluronic acid.

7. The cellular support system of claim 6, wherein the hyaluronic acid has a molecular weight of greater than or equal to about 15 kDa to less than or equal to about 15,000 kDa.

8. The cellular support system of claim 1, wherein a mass ratio of the at least one extracellular matrix protein to the at least one glycan is greater than or equal to about 1:1 to less than or equal to about 1:3.

9. The cellular support system of claim 1, wherein a mass ratio of the at least one extracellular matrix protein to the at least one glycan is greater than or equal to about 1:1.5 to less than or equal to about 1:2.5.

10. The cellular support system of claim 1, wherein the three-dimensional scaffold structure is formed from a material selected from the group consisting of: a metal material, a polymeric material, a composite material, a ceramic material, a biologically-derived material, and combinations thereof.

11. The cellular support system of claim 1, wherein the three-dimensional scaffold structure comprises a polymer and is formed from a polymeric precursor or is a polymer selected from the group consisting of: polylactic acid, polyglycolide, polycaprolactone, poly(lactide-co-glycolide), poly(lactide-co-caprolactone), polyethylene glycol, starches, polydimethylsiloxane, polyurethanes, polyolefins, polyamides, celluloses, lignins, biodegradable polyesters, polystyrene, and combinations thereof.

12. The cellular support system of claim 1, wherein the suspended fibril has an average diameter of greater than or equal to about 1 micrometer to less than or equal to about 1.5 micrometers.

13. The cellular support system of claim 1, wherein the at least one void comprises a plurality of distinct fibrils spanning across the at least one void in the three-dimensional scaffold structure to define a fibrillar network in the at least one void.

14. The cellular support system of claim 1, wherein the suspended fibril has a length of greater than or equal to about 1 mm.

15. A cellular support system comprising:

a three-dimensional scaffold structure comprising at least one void; and a fibrillar network comprising a plurality of suspended fibrils spanning across the at least one void in the three-dimensional scaffold structure, wherein each of the suspended fibrils comprises fibronectin conjugated by at least one disulfide or thiol group to functionalized and hyaluronic acid and the fibrillar network is capable of supporting cells and promoting three-dimensional cellular growth.

16. The cellular support system of claim 15, wherein the void has a major dimension of greater than or equal to about 0.1 micrometers to less than or equal to about 5 centimeters.

17. The cellular support system of claim 15, wherein at least one of the plurality of suspended fibrils further comprises collagen.

18. The cellular support system of claim 15, wherein the hyaluronic acid has a molecular weight of greater than or equal to about 15 kDa to less than or equal to about 15,000 kDa.

19. The cellular support system of claim 15, wherein a mass ratio of fibronectin to hyaluronic acid is greater than or equal to about 1:1 to less than or equal to about 1:3.

20. The cellular support system of claim 15, wherein a mass ratio of fibronectin to the hyaluronic acid is greater than or equal to about 1:1.5 to less than or equal to about 1:2.5.

21. The cellular support system of claim 15, wherein each of the suspended fibrils has an average diameter of greater than or equal to about 1 micrometer to less than or equal to about 1.5 micrometers and a length of greater than or equal to about 1 mm.

* * * * *